United States Patent
Dulin et al.

(10) Patent No.: US 12,232,820 B2
(45) Date of Patent: Feb. 25, 2025

(54) EXTENDED REALITY SYSTEMS WITH THREE-DIMENSIONAL VISUALIZATIONS OF MEDICAL IMAGE SCAN SLICES

(71) Applicant: GLOBUS MEDICAL, INC., Audubon, PA (US)

(72) Inventors: Isaac Dulin, Somerville, MA (US); Tom Calloway, Pelham, NH (US)

(73) Assignee: Globus Medical, Inc., Audubon, PA (US)

( * ) Notice: Subject to any disclaimer, the term of this patent is extended or adjusted under 35 U.S.C. 154(b) by 404 days.

(21) Appl. No.: 17/540,319

(22) Filed: Dec. 2, 2021

(65) Prior Publication Data

US 2023/0165640 A1  Jun. 1, 2023

Related U.S. Application Data

(63) Continuation of application No. 17/539,796, filed on Dec. 1, 2021.

(51) Int. Cl.
*A61B 34/20* (2016.01)
*A61B 34/10* (2016.01)
(Continued)

(52) U.S. Cl.
CPC .............. *A61B 34/20* (2016.02); *A61B 34/10* (2016.02); *A61B 90/361* (2016.02); *A61B 90/37* (2016.02);
(Continued)

(58) Field of Classification Search
CPC ....... A61B 34/20; A61B 34/10; A61B 90/361; A61B 90/37; A61B 2034/102; A61B 2034/105; A61B 2034/2055; A61B 2090/365; A61B 2090/367; A61B 2090/372; A61B 34/32; A61B 2017/00203; A61B 2017/00207; A61B 2090/3979; A61B 2090/502; A61B 2090/374; A61B 2034/2048; A61B 2090/368; A61B 2090/376; A61B 2090/3762; A61B 2090/3983; G06F 3/011; G06T 7/20; G06T 7/70; G06T 17/00; G06T 19/006;
(Continued)

(56) References Cited

U.S. PATENT DOCUMENTS 4,150,293 A  4/1979  Franke
5,246,010 A  9/1993  Gazzara et al.
(Continued)

OTHER PUBLICATIONS

US 8,231,638 B2, 07/2012, Swarup et al. (withdrawn)

*Primary Examiner* — Alexei Bykhovski

(57) ABSTRACT

A navigated surgery system includes at least one processor that is operative to obtain a 2D medical image slice of anatomical structure of a patient. The operations further obtain a 3D graphical model of anatomical structure. The operations determine a pose of a virtual cross-sectional plane extending through the 3D graphical model of the anatomical structure that corresponds to the anatomical structure of the 2D medical image slice. The operations control the XR headset to display the 2D medical image slice of the anatomical structure of the patient, display the 3D graphical model of the anatomical structure, and display a graphical object oriented with the pose relative to the 3D graphical model of the anatomical structure.

12 Claims, 15 Drawing Sheets

(51) Int. Cl.
  *A61B 90/00* (2016.01)
  *G06F 3/01* (2006.01)
  *G06T 7/20* (2017.01)
  *G06T 7/70* (2017.01)
  *G06T 17/00* (2006.01)
  *G06T 19/00* (2011.01)
  *G06T 19/20* (2011.01)

(52) U.S. Cl.
  CPC ............... *G06F 3/011* (2013.01); *G06T 7/20* (2013.01); *G06T 7/70* (2017.01); *G06T 17/00* (2013.01); *G06T 19/006* (2013.01); *G06T 19/20* (2013.01); *A61B 2034/102* (2016.02); *A61B 2034/105* (2016.02); *A61B 2034/2055* (2016.02); *A61B 2090/365* (2016.02); *A61B 2090/367* (2016.02); *A61B 2090/372* (2016.02); *G06T 2207/30012* (2013.01); *G06T 2207/30052* (2013.01); *G06T 2210/41* (2013.01); *G06T 2219/008* (2013.01); *G06T 2219/2004* (2013.01); *G06T 2219/2012* (2013.01); *G06T 2219/2016* (2013.01)

(58) Field of Classification Search
  CPC ........... G06T 19/20; G06T 2207/30012; G06T 2207/30052; G06T 2210/41; G06T 2219/008; G06T 2219/2004; G06T 2219/2012; G06T 2219/2016; G06T 19/00
  See application file for complete search history.

(56) References Cited

U.S. PATENT DOCUMENTS

| | | | |
|---|---|---|---|
| 5,354,314 | A | 10/1994 | Hardy et al. |
| 5,397,323 | A | 3/1995 | Taylor et al. |
| 5,598,453 | A | 1/1997 | Baba et al. |
| 5,772,594 | A | 6/1998 | Barrick |
| 5,791,908 | A | 8/1998 | Gillio |
| 5,820,559 | A | 10/1998 | Ng et al. |
| 5,825,982 | A | 10/1998 | Wright et al. |
| 5,887,121 | A | 3/1999 | Funda et al. |
| 5,911,449 | A | 6/1999 | Daniele et al. |
| 5,951,475 | A | 9/1999 | Gueziec et al. |
| 5,987,960 | A | 11/1999 | Messner et al. |
| 6,012,216 | A | 1/2000 | Esteves et al. |
| 6,031,888 | A | 2/2000 | Ivan et al. |
| 6,033,415 | A | 3/2000 | Mittelstadt et al. |
| 6,080,181 | A | 6/2000 | Jensen et al. |
| 6,106,511 | A | 8/2000 | Jensen |
| 6,122,541 | A | 9/2000 | Cosman et al. |
| 6,144,875 | A | 11/2000 | Schweikard et al. |
| 6,157,853 | A | 12/2000 | Blume et al. |
| 6,167,145 | A | 12/2000 | Foley et al. |
| 6,167,292 | A | 12/2000 | Badano et al. |
| 6,201,984 | B1 | 3/2001 | Funda et al. |
| 6,203,196 | B1 | 3/2001 | Meyer et al. |
| 6,205,411 | B1 | 3/2001 | DiGioia, III et al. |
| 6,212,419 | B1 | 4/2001 | Blume et al. |
| 6,231,565 | B1 | 5/2001 | Tovey et al. |
| 6,236,875 | B1 | 5/2001 | Bucholz et al. |
| 6,246,900 | B1 | 6/2001 | Cosman et al. |
| 6,301,495 | B1 | 10/2001 | Gueziec et al. |
| 6,306,126 | B1 | 10/2001 | Montezuma |
| 6,312,435 | B1 | 11/2001 | Wallace et al. |
| 6,314,311 | B1 | 11/2001 | Williams et al. |
| 6,320,929 | B1 | 11/2001 | Von Der Haar |
| 6,322,567 | B1 | 11/2001 | Mittelstadt et al. |
| 6,325,808 | B1 | 12/2001 | Bernard et al. |
| 6,340,363 | B1 | 1/2002 | Bolger et al. |
| 6,377,011 | B1 | 4/2002 | Ben-Ur |
| 6,379,302 | B1 | 4/2002 | Kessman et al. |
| 6,402,762 | B2 | 6/2002 | Hunter et al. |
| 6,424,885 | B1 | 7/2002 | Niemeyer et al. |
| 6,447,503 | B1 | 9/2002 | Wynne et al. |
| 6,451,027 | B1 | 9/2002 | Cooper et al. |
| 6,477,400 | B1 | 11/2002 | Barrick |
| 6,484,049 | B1 | 11/2002 | Seeley et al. |
| 6,487,267 | B1 | 11/2002 | Wolter |
| 6,490,467 | B1 | 12/2002 | Bucholz et al. |
| 6,490,475 | B1 | 12/2002 | Seeley et al. |
| 6,499,488 | B1 | 12/2002 | Hunter et al. |
| 6,501,981 | B1 | 12/2002 | Schweikard et al. |
| 6,507,751 | B2 | 1/2003 | Blume et al. |
| 6,535,756 | B1 | 3/2003 | Simon et al. |
| 6,560,354 | B1 | 5/2003 | Maurer, Jr. et al. |
| 6,565,554 | B1 | 5/2003 | Niemeyer |
| 6,587,750 | B2 | 7/2003 | Gerbi et al. |
| 6,614,453 | B1 | 9/2003 | Suri et al. |
| 6,614,871 | B1 | 9/2003 | Kobiki et al. |
| 6,619,840 | B2 | 9/2003 | Rasche et al. |
| 6,636,757 | B1 | 10/2003 | Jascob et al. |
| 6,645,196 | B1 | 11/2003 | Nixon et al. |
| 6,666,579 | B2 | 12/2003 | Jensen |
| 6,669,635 | B2 | 12/2003 | Kessman et al. |
| 6,701,173 | B2 | 3/2004 | Nowinski et al. |
| 6,757,068 | B2 | 6/2004 | Foxlin |
| 6,782,287 | B2 | 8/2004 | Grzeszczuk et al. |
| 6,783,524 | B2 | 8/2004 | Anderson et al. |
| 6,786,896 | B1 | 9/2004 | Madhani et al. |
| 6,788,018 | B1 | 9/2004 | Blumenkranz |
| 6,804,581 | B2 | 10/2004 | Wang et al. |
| 6,823,207 | B1 | 11/2004 | Jensen et al. |
| 6,827,351 | B2 | 12/2004 | Graziani et al. |
| 6,837,892 | B2 | 1/2005 | Shoham |
| 6,839,612 | B2 | 1/2005 | Sanchez et al. |
| 6,856,826 | B2 | 2/2005 | Seeley et al. |
| 6,856,827 | B2 | 2/2005 | Seeley et al. |
| 6,879,880 | B2 | 4/2005 | Nowlin et al. |
| 6,892,090 | B2 | 5/2005 | Verard et al. |
| 6,920,347 | B2 | 7/2005 | Simon et al. |
| 6,922,632 | B2 | 7/2005 | Foxlin |
| 6,968,224 | B2 | 11/2005 | Kessman et al. |
| 6,978,166 | B2 | 12/2005 | Foley et al. |
| 6,988,009 | B2 | 1/2006 | Grimm et al. |
| 6,991,627 | B2 | 1/2006 | Madhani et al. |
| 6,996,487 | B2 | 2/2006 | Jutras et al. |
| 6,999,852 | B2 | 2/2006 | Green |
| 7,007,699 | B2 | 3/2006 | Martinelli et al. |
| 7,016,457 | B1 | 3/2006 | Senzig et al. |
| 7,043,961 | B2 | 5/2006 | Pandey et al. |
| 7,062,006 | B1 | 6/2006 | Pelc et al. |
| 7,063,705 | B2 | 6/2006 | Young et al. |
| 7,072,707 | B2 | 7/2006 | Galloway, Jr. et al. |
| 7,083,615 | B2 | 8/2006 | Peterson et al. |
| 7,097,640 | B2 | 8/2006 | Wang et al. |
| 7,099,428 | B2 | 8/2006 | Clinthorne et al. |
| 7,108,421 | B2 | 9/2006 | Gregerson et al. |
| 7,130,676 | B2 | 10/2006 | Barrick |
| 7,139,418 | B2 | 11/2006 | Abovitz et al. |
| 7,139,601 | B2 | 11/2006 | Bucholz et al. |
| 7,155,316 | B2 | 12/2006 | Sutherland et al. |
| 7,164,968 | B2 | 1/2007 | Treat et al. |
| 7,167,738 | B2 | 1/2007 | Schweikard et al. |
| 7,169,141 | B2 | 1/2007 | Brock et al. |
| 7,172,627 | B2 | 2/2007 | Fiere et al. |
| 7,194,120 | B2 | 3/2007 | Wicker et al. |
| 7,197,107 | B2 | 3/2007 | Arai et al. |
| 7,231,014 | B2 | 6/2007 | Levy |
| 7,231,063 | B2 | 6/2007 | Naimark et al. |
| 7,239,940 | B2 | 7/2007 | Wang et al. |
| 7,248,914 | B2 | 7/2007 | Hastings et al. |
| 7,301,648 | B2 | 11/2007 | Foxlin |
| 7,302,288 | B1 | 11/2007 | Schellenberg |
| 7,313,430 | B2 | 12/2007 | Urquhart et al. |
| 7,318,805 | B2 | 1/2008 | Schweikard et al. |
| 7,318,827 | B2 | 1/2008 | Leitner et al. |
| 7,319,897 | B2 | 1/2008 | Leitner et al. |
| 7,324,623 | B2 | 1/2008 | Heuscher et al. |
| 7,327,865 | B2 | 2/2008 | Fu et al. |
| 7,331,967 | B2 | 2/2008 | Lee et al. |
| 7,333,642 | B2 | 2/2008 | Green |
| 7,339,341 | B2 | 3/2008 | Oleynikov et al. |

(56) References Cited

U.S. PATENT DOCUMENTS

| | | |
|---|---|---|
| 7,366,562 B2 | 4/2008 | Dukesherer et al. |
| 7,379,790 B2 | 5/2008 | Toth et al. |
| 7,386,365 B2 | 6/2008 | Nixon |
| 7,422,592 B2 | 9/2008 | Morley et al. |
| 7,435,216 B2 | 10/2008 | Kwon et al. |
| 7,440,793 B2 | 10/2008 | Chauhan et al. |
| 7,460,637 B2 | 12/2008 | Clinthorne et al. |
| 7,466,303 B2 | 12/2008 | Yi et al. |
| 7,493,153 B2 | 2/2009 | Ahmed et al. |
| 7,505,617 B2 | 3/2009 | Fu et al. |
| 7,533,892 B2 | 5/2009 | Schena et al. |
| 7,542,791 B2 | 6/2009 | Mire et al. |
| 7,555,331 B2 | 6/2009 | Viswanathan |
| 7,567,834 B2 | 7/2009 | Clayton et al. |
| 7,594,912 B2 | 9/2009 | Cooper et al. |
| 7,606,613 B2 | 10/2009 | Simon et al. |
| 7,607,440 B2 | 10/2009 | Coste-Maniere et al. |
| 7,623,902 B2 | 11/2009 | Pacheco |
| 7,630,752 B2 | 12/2009 | Viswanathan |
| 7,630,753 B2 | 12/2009 | Simon et al. |
| 7,643,862 B2 | 1/2010 | Schoenefeld |
| 7,660,623 B2 | 2/2010 | Hunter et al. |
| 7,661,881 B2 | 2/2010 | Gregerson et al. |
| 7,683,331 B2 | 3/2010 | Chang |
| 7,683,332 B2 | 3/2010 | Chang |
| 7,689,320 B2 | 3/2010 | Prisco et al. |
| 7,691,098 B2 | 4/2010 | Wallace et al. |
| 7,702,379 B2 | 4/2010 | Avinash et al. |
| 7,702,477 B2 | 4/2010 | Tuemmler et al. |
| 7,711,083 B2 | 5/2010 | Heigl et al. |
| 7,711,406 B2 | 5/2010 | Kuhn et al. |
| 7,720,523 B2 | 5/2010 | Omernick et al. |
| 7,725,253 B2 | 5/2010 | Foxlin |
| 7,726,171 B2 | 6/2010 | Langlotz et al. |
| 7,742,801 B2 | 6/2010 | Neubauer et al. |
| 7,751,865 B2 | 7/2010 | Jascob et al. |
| 7,760,849 B2 | 7/2010 | Zhang |
| 7,762,825 B2 | 7/2010 | Burbank et al. |
| 7,763,015 B2 | 7/2010 | Cooper et al. |
| 7,787,699 B2 | 8/2010 | Mahesh et al. |
| 7,796,728 B2 | 9/2010 | Bergfjord |
| 7,813,838 B2 | 10/2010 | Sommer |
| 7,818,044 B2 | 10/2010 | Dukesherer et al. |
| 7,819,859 B2 | 10/2010 | Prisco et al. |
| 7,824,401 B2 | 11/2010 | Manzo et al. |
| 7,831,294 B2 | 11/2010 | Viswanathan |
| 7,834,484 B2 | 11/2010 | Sartor |
| 7,835,557 B2 | 11/2010 | Kendrick et al. |
| 7,835,778 B2 | 11/2010 | Foley et al. |
| 7,835,784 B2 | 11/2010 | Mire et al. |
| 7,840,253 B2 | 11/2010 | Tremblay et al. |
| 7,840,256 B2 | 11/2010 | Lakin et al. |
| 7,843,158 B2 | 11/2010 | Prisco |
| 7,844,320 B2 | 11/2010 | Shahidi |
| 7,853,305 B2 | 12/2010 | Simon et al. |
| 7,853,313 B2 | 12/2010 | Thompson |
| 7,865,269 B2 | 1/2011 | Prisco et al. |
| D631,966 S | 2/2011 | Perloff et al. |
| 7,879,045 B2 | 2/2011 | Gielen et al. |
| 7,881,767 B2 | 2/2011 | Strommer et al. |
| 7,881,770 B2 | 2/2011 | Melkent et al. |
| 7,886,743 B2 | 2/2011 | Cooper et al. |
| RE42,194 E | 3/2011 | Foley et al. |
| RE42,226 E | 3/2011 | Foley et al. |
| 7,900,524 B2 | 3/2011 | Calloway et al. |
| 7,907,166 B2 | 3/2011 | Lamprecht et al. |
| 7,909,122 B2 | 3/2011 | Schena et al. |
| 7,925,653 B2 | 4/2011 | Saptharishi |
| 7,930,065 B2 | 4/2011 | Arkin et al. |
| 7,935,130 B2 | 5/2011 | Williams |
| 7,940,999 B2 | 5/2011 | Liao et al. |
| 7,945,012 B2 | 5/2011 | Ye et al. |
| 7,945,021 B2 | 5/2011 | Shapiro et al. |
| 7,953,470 B2 | 5/2011 | Vetter et al. |
| 7,954,397 B2 | 6/2011 | Choi et al. |
| 7,971,341 B2 | 7/2011 | Dukesherer et al. |
| 7,974,674 B2 | 7/2011 | Hauck et al. |
| 7,974,677 B2 | 7/2011 | Mire et al. |
| 7,974,681 B2 | 7/2011 | Wallace et al. |
| 7,979,157 B2 | 7/2011 | Anvari |
| 7,983,733 B2 | 7/2011 | Viswanathan |
| 7,988,215 B2 | 8/2011 | Seibold |
| 7,996,110 B2 | 8/2011 | Lipow et al. |
| 8,004,121 B2 | 8/2011 | Sartor |
| 8,004,229 B2 | 8/2011 | Nowlin et al. |
| 8,010,177 B2 | 8/2011 | Csavoy et al. |
| 8,019,045 B2 | 9/2011 | Kato |
| 8,021,310 B2 | 9/2011 | Sanborn et al. |
| 8,035,685 B2 | 10/2011 | Jensen |
| 8,046,054 B2 | 10/2011 | Kim et al. |
| 8,046,057 B2 | 10/2011 | Clarke |
| 8,052,688 B2 | 11/2011 | Wolf, II |
| 8,054,184 B2 | 11/2011 | Cline et al. |
| 8,054,752 B2 | 11/2011 | Druke et al. |
| 8,057,397 B2 | 11/2011 | Li et al. |
| 8,057,407 B2 | 11/2011 | Martinelli et al. |
| 8,062,288 B2 | 11/2011 | Cooper et al. |
| 8,062,375 B2 | 11/2011 | Glerum et al. |
| 8,066,524 B2 | 11/2011 | Burbank et al. |
| 8,073,335 B2 | 12/2011 | Labonville et al. |
| 8,079,950 B2 | 12/2011 | Stern et al. |
| 8,086,299 B2 | 12/2011 | Adler et al. |
| 8,092,370 B2 | 1/2012 | Roberts et al. |
| 8,098,914 B2 | 1/2012 | Liao et al. |
| 8,100,950 B2 | 1/2012 | St. Clair et al. |
| 8,105,320 B2 | 1/2012 | Manzo |
| 8,108,025 B2 | 1/2012 | Csavoy et al. |
| 8,109,877 B2 | 2/2012 | Moctezuma de la Barrera et al. |
| 8,112,292 B2 | 2/2012 | Simon |
| 8,116,430 B1 | 2/2012 | Shapiro et al. |
| 8,120,301 B2 | 2/2012 | Goldberg et al. |
| 8,121,249 B2 | 2/2012 | Wang et al. |
| 8,123,675 B2 | 2/2012 | Funda et al. |
| 8,133,229 B1 | 3/2012 | Bonutti |
| 8,142,420 B2 | 3/2012 | Schena |
| 8,147,494 B2 | 4/2012 | Leitner et al. |
| 8,150,494 B2 | 4/2012 | Simon et al. |
| 8,150,497 B2 | 4/2012 | Gielen et al. |
| 8,150,498 B2 | 4/2012 | Gielen et al. |
| 8,165,658 B2 | 4/2012 | Waynik et al. |
| 8,170,313 B2 | 5/2012 | Kendrick et al. |
| 8,179,073 B2 | 5/2012 | Farritor et al. |
| 8,182,476 B2 | 5/2012 | Julian et al. |
| 8,184,880 B2 | 5/2012 | Zhao et al. |
| 8,202,278 B2 | 6/2012 | Orban, III et al. |
| 8,208,708 B2 | 6/2012 | Homan et al. |
| 8,208,988 B2 | 6/2012 | Jenser |
| 8,219,177 B2 | 7/2012 | Smith et al. |
| 8,219,178 B2 | 7/2012 | Smith et al. |
| 8,220,468 B2 | 7/2012 | Cooper et al. |
| 8,224,024 B2 | 7/2012 | Foxlin et al. |
| 8,224,484 B2 | 7/2012 | Swarup et al. |
| 8,225,798 B2 | 7/2012 | Baldwin et al. |
| 8,228,368 B2 | 7/2012 | Zhao et al. |
| 8,231,610 B2 | 7/2012 | Jo et al. |
| 8,263,933 B2 | 7/2012 | Hartmann et al. |
| 8,239,001 B2 | 8/2012 | Verard et al. |
| 8,241,271 B2 | 8/2012 | Millman et al. |
| 8,248,413 B2 | 8/2012 | Gattani et al. |
| 8,256,319 B2 | 9/2012 | Cooper et al. |
| 8,271,069 B2 | 9/2012 | Jascob et al. |
| 8,271,130 B2 | 9/2012 | Hourtash |
| 8,281,670 B2 | 10/2012 | Larkin et al. |
| 8,282,653 B2 | 10/2012 | Nelson et al. |
| 8,301,226 B2 | 10/2012 | Csavoy et al. |
| 8,311,611 B2 | 11/2012 | Csavoy et al. |
| 8,320,991 B2 | 11/2012 | Jascob et al. |
| 8,332,012 B2 | 12/2012 | Kienzle, III |
| 8,333,755 B2 | 12/2012 | Cooper et al. |
| 8,335,552 B2 | 12/2012 | Stiles |
| 8,335,557 B2 | 12/2012 | Maschke |
| 8,348,931 B2 | 1/2013 | Cooper et al. |
| 8,353,963 B2 | 1/2013 | Glerum |
| 8,358,818 B2 | 1/2013 | Miga et al. |

(56) References Cited

U.S. PATENT DOCUMENTS

| | | | |
|---|---|---|---|
| 8,359,730 B2 | 1/2013 | Burg et al. |
| 8,374,673 B2 | 2/2013 | Adcox et al. |
| 8,374,723 B2 | 2/2013 | Zhao et al. |
| 8,379,791 B2 | 2/2013 | Forthmann et al. |
| 8,386,019 B2 | 2/2013 | Camus et al. |
| 8,392,022 B2 | 3/2013 | Ortmaier et al. |
| 8,394,099 B2 | 3/2013 | Patwardhan |
| 8,395,342 B2 | 3/2013 | Prisco |
| 8,398,634 B2 | 3/2013 | Manzo et al. |
| 8,400,094 B2 | 3/2013 | Schena |
| 8,414,957 B2 | 4/2013 | Enzerink et al. |
| 8,418,073 B2 | 4/2013 | Mohr et al. |
| 8,450,694 B2 | 5/2013 | Baviera et al. |
| 8,452,447 B2 | 5/2013 | Nixon |
| RE44,305 E | 6/2013 | Foley et al. |
| 8,462,911 B2 | 6/2013 | Vesel et al. |
| 8,465,476 B2 | 6/2013 | Rogers et al. |
| 8,465,771 B2 | 6/2013 | Wan et al. |
| 8,467,851 B2 | 6/2013 | Mire et al. |
| 8,467,852 B2 | 6/2013 | Csavoy et al. |
| 8,469,947 B2 | 6/2013 | Devengenzo et al. |
| RE44,392 E | 7/2013 | Hynes |
| 8,483,434 B2 | 7/2013 | Buehner et al. |
| 8,483,800 B2 | 7/2013 | Jensen et al. |
| 8,486,532 B2 | 7/2013 | Enzerink et al. |
| 8,489,235 B2 | 7/2013 | Moll et al. |
| 8,500,722 B2 | 8/2013 | Cooper |
| 8,500,728 B2 | 8/2013 | Newton et al. |
| 8,504,201 B2 | 8/2013 | Moll et al. |
| 8,506,555 B2 | 8/2013 | Ruiz Morales |
| 8,506,556 B2 | 8/2013 | Schena |
| 8,508,173 B2 | 8/2013 | Goldberg et al. |
| 8,512,318 B2 | 8/2013 | Tovey et al. |
| 8,515,576 B2 | 8/2013 | Lipow et al. |
| 8,518,120 B2 | 8/2013 | Glerum et al. |
| 8,521,331 B2 | 8/2013 | Itkowitz |
| 8,526,688 B2 | 9/2013 | Groszmann et al. |
| 8,526,700 B2 | 9/2013 | Issacs |
| 8,527,094 B2 | 9/2013 | Kumar et al. |
| 8,528,440 B2 | 9/2013 | Morley et al. |
| 8,532,741 B2 | 9/2013 | Heruth et al. |
| 8,541,970 B2 | 9/2013 | Nowlin et al. |
| 8,548,563 B2 | 10/2013 | Simon et al. |
| 8,549,732 B2 | 10/2013 | Burg et al. |
| 8,551,114 B2 | 10/2013 | Ramos de la Pena |
| 8,551,116 B2 | 10/2013 | Julian et al. |
| 8,556,807 B2 | 10/2013 | Scott et al. |
| 8,556,979 B2 | 10/2013 | Glerum et al. |
| 8,560,118 B2 | 10/2013 | Green et al. |
| 8,561,473 B2 | 10/2013 | Blumenkranz |
| 8,562,594 B2 | 10/2013 | Cooper et al. |
| 8,571,638 B2 | 10/2013 | Shoham |
| 8,571,710 B2 | 10/2013 | Coste-Maniere et al. |
| 8,573,465 B2 | 11/2013 | Shelton, IV |
| 8,574,303 B2 | 11/2013 | Sharkey et al. |
| 8,585,420 B2 | 11/2013 | Burbank et al. |
| 8,594,841 B2 | 11/2013 | Zhao et al. |
| 8,597,198 B2 | 12/2013 | Sanborn et al. |
| 8,600,478 B2 | 12/2013 | Verard et al. |
| 8,603,077 B2 | 12/2013 | Cooper et al. |
| 8,611,985 B2 | 12/2013 | Lavallee et al. |
| 8,613,230 B2 | 12/2013 | Blumenkranz et al. |
| 8,621,939 B2 | 1/2014 | Blumenkranz et al. |
| 8,624,537 B2 | 1/2014 | Nowlin et al. |
| 8,630,389 B2 | 1/2014 | Kato |
| 8,634,897 B2 | 1/2014 | Simon et al. |
| 8,634,957 B2 | 1/2014 | Toth et al. |
| 8,638,056 B2 | 1/2014 | Goldberg et al. |
| 8,638,057 B2 | 1/2014 | Goldberg et al. |
| 8,639,000 B2 | 1/2014 | Zhao et al. |
| 8,641,726 B2 | 2/2014 | Bonutti |
| 8,644,907 B2 | 2/2014 | Hartmann et al. |
| 8,657,809 B2 | 2/2014 | Schoepp |
| 8,660,635 B2 | 2/2014 | Simon et al. |
| 8,666,544 B2 | 3/2014 | Moll et al. |
| 8,675,939 B2 | 3/2014 | Moctezuma de la Barrera |
| 8,678,647 B2 | 3/2014 | Gregerson et al. |
| 8,679,125 B2 | 3/2014 | Smith et al. |
| 8,679,183 B2 | 3/2014 | Glerum et al. |
| 8,682,413 B2 | 3/2014 | Lloyd |
| 8,684,253 B2 | 4/2014 | Giordano et al. |
| 8,685,098 B2 | 4/2014 | Glerum et al. |
| 8,693,730 B2 | 4/2014 | Umasuthan et al. |
| 8,694,075 B2 | 4/2014 | Groszmann et al. |
| 8,696,458 B2 | 4/2014 | Foxlin et al. |
| 8,700,123 B2 | 4/2014 | Okamura et al. |
| 8,706,086 B2 | 4/2014 | Glerum |
| 8,706,185 B2 | 4/2014 | Foley et al. |
| 8,706,301 B2 | 4/2014 | Zhao et al. |
| 8,717,430 B2 | 5/2014 | Simon et al. |
| 8,727,618 B2 | 5/2014 | Maschke et al. |
| 8,734,432 B2 | 5/2014 | Tuma et al. |
| 8,738,115 B2 | 5/2014 | Amberg et al. |
| 8,738,181 B2 | 5/2014 | Greer et al. |
| 8,740,882 B2 | 6/2014 | Jun et al. |
| 8,746,252 B2 | 6/2014 | McGrogan et al. |
| 8,749,189 B2 | 6/2014 | Nowlin et al. |
| 8,749,190 B2 | 6/2014 | Nowlin et al. |
| 8,761,930 B2 | 6/2014 | Nixon |
| 8,764,448 B2 | 7/2014 | Yang et al. |
| 8,771,170 B2 | 7/2014 | Mesallum et al. |
| 8,781,186 B2 | 7/2014 | Clements et al. |
| 8,781,630 B2 | 7/2014 | Banks et al. |
| 8,784,385 B2 | 7/2014 | Boyden et al. |
| 8,786,241 B2 | 7/2014 | Nowlin et al. |
| 8,787,520 B2 | 7/2014 | Baba |
| 8,792,704 B2 | 7/2014 | Isaacs |
| 8,798,231 B2 | 8/2014 | Notohara et al. |
| 8,800,838 B2 | 8/2014 | Shelton, IV |
| 8,808,164 B2 | 8/2014 | Hoffman et al. |
| 8,812,077 B2 | 8/2014 | Dempsey |
| 8,814,793 B2 | 8/2014 | Brabrand |
| 8,816,628 B2 | 8/2014 | Nowlin et al. |
| 8,818,105 B2 | 8/2014 | Myronenko et al. |
| 8,820,605 B2 | 9/2014 | Shelton, IV |
| 8,821,511 B2 | 9/2014 | von Jako et al. |
| 8,823,308 B2 | 9/2014 | Nowlin et al. |
| 8,827,996 B2 | 9/2014 | Scott et al. |
| 8,828,024 B2 | 9/2014 | Farritor et al. |
| 8,830,224 B2 | 9/2014 | Zhao et al. |
| 8,834,489 B2 | 9/2014 | Cooper et al. |
| 8,834,490 B2 | 9/2014 | Bonutti |
| 8,838,270 B2 | 9/2014 | Druke et al. |
| 8,844,789 B2 | 9/2014 | Shelton, IV et al. |
| 8,855,822 B2 | 10/2014 | Bartol et al. |
| 8,858,598 B2 | 10/2014 | Seifert et al. |
| 8,860,753 B2 | 10/2014 | Bhandarkar et al. |
| 8,864,751 B2 | 10/2014 | Prisco et al. |
| 8,864,798 B2 | 10/2014 | Weiman et al. |
| 8,864,833 B2 | 10/2014 | Glerum et al. |
| 8,867,703 B2 | 10/2014 | Shapiro et al. |
| 8,870,880 B2 | 10/2014 | Himmelberger et al. |
| 8,876,866 B2 | 11/2014 | Zappacosta et al. |
| 8,880,223 B2 | 11/2014 | Raj et al. |
| 8,882,803 B2 | 11/2014 | Iott et al. |
| 8,883,210 B1 | 11/2014 | Truncale et al. |
| 8,888,821 B2 | 11/2014 | Rezach et al. |
| 8,888,853 B2 | 11/2014 | Glerum et al. |
| 8,888,854 B2 | 11/2014 | Glerum et al. |
| 8,894,652 B2 | 11/2014 | Seifert et al. |
| 8,894,688 B2 | 11/2014 | Suh |
| 8,894,691 B2 | 11/2014 | Iott et al. |
| 8,906,069 B2 | 12/2014 | Hansell et al. |
| 8,964,934 B2 | 2/2015 | Ein-Gal |
| 8,992,580 B2 | 3/2015 | Bar et al. |
| 8,996,169 B2 | 3/2015 | Lightcap et al. |
| 9,001,963 B2 | 4/2015 | Sowards-Emmerd et al. |
| 9,002,076 B2 | 4/2015 | Khadem et al. |
| 9,044,190 B2 | 6/2015 | Rubner et al. |
| 9,107,683 B2 | 8/2015 | Hourtash et al. |
| 9,125,556 B2 | 9/2015 | Zehavi et al. |
| 9,131,986 B2 | 9/2015 | Greer et al. |
| 9,215,968 B2 | 12/2015 | Schostek et al. |
| 9,308,050 B2 | 4/2016 | Kostrzewski et al. |

(56) References Cited

U.S. PATENT DOCUMENTS

| | | |
|---|---|---|
| 9,380,984 B2 | 7/2016 | Li et al. |
| 9,393,039 B2 | 7/2016 | Lechner et al. |
| 9,398,886 B2 | 7/2016 | Gregerson et al. |
| 9,398,890 B2 | 7/2016 | Dong et al. |
| 9,414,859 B2 | 8/2016 | Ballard et al. |
| 9,420,975 B2 | 8/2016 | Gutfleisch et al. |
| 9,492,235 B2 | 11/2016 | Hourtash et al. |
| 9,592,096 B2 | 3/2017 | Maillet et al. |
| 9,750,465 B2 | 9/2017 | Engel et al. |
| 9,757,203 B2 | 9/2017 | Hourtash et al. |
| 9,795,354 B2 | 10/2017 | Menegaz et al. |
| 9,814,535 B2 | 11/2017 | Bar et al. |
| 9,820,783 B2 | 11/2017 | Donner et al. |
| 9,833,265 B2 | 11/2017 | Donner et al. |
| 9,848,922 B2 | 12/2017 | Tohmeh et al. |
| 9,925,011 B2 | 3/2018 | Gombert et al. |
| 9,931,025 B1 | 4/2018 | Graetzel et al. |
| 10,034,717 B2 | 7/2018 | Miller et al. |
| 2001/0036302 A1 | 11/2001 | Miller |
| 2002/0035321 A1 | 3/2002 | Bucholz et al. |
| 2004/0068172 A1 | 4/2004 | Nowinski et al. |
| 2004/0076259 A1 | 4/2004 | Jensen et al. |
| 2005/0096502 A1 | 5/2005 | Khalili |
| 2005/0143651 A1 | 6/2005 | Verard et al. |
| 2005/0171558 A1 | 8/2005 | Abovitz et al. |
| 2006/0100610 A1 | 5/2006 | Wallace et al. |
| 2006/0173329 A1 | 8/2006 | Marquart et al. |
| 2006/0184396 A1 | 8/2006 | Dennis et al. |
| 2006/0241416 A1 | 10/2006 | Marquart et al. |
| 2006/0291612 A1 | 12/2006 | Nishide et al. |
| 2007/0015987 A1 | 1/2007 | Benlloch Baviera et al. |
| 2007/0021738 A1 | 1/2007 | Hasser et al. |
| 2007/0038059 A1 | 2/2007 | Sheffer et al. |
| 2007/0073133 A1 | 3/2007 | Schoenefeld |
| 2007/0156121 A1 | 7/2007 | Millman et al. |
| 2007/0156157 A1 | 7/2007 | Nahum et al. |
| 2007/0167712 A1 | 7/2007 | Keglovich et al. |
| 2007/0233238 A1 | 10/2007 | Huynh et al. |
| 2007/0238981 A1* | 10/2007 | Zhu ................. A61B 34/20 600/424 |
| 2008/0004523 A1 | 1/2008 | Jensen |
| 2008/0013809 A1 | 1/2008 | Zhu et al. |
| 2008/0033283 A1 | 2/2008 | Dellaca et al. |
| 2008/0046122 A1 | 2/2008 | Manzo et al. |
| 2008/0082109 A1 | 4/2008 | Moll et al. |
| 2008/0108912 A1 | 5/2008 | Node-Langlois |
| 2008/0108991 A1 | 5/2008 | von Jako |
| 2008/0109012 A1 | 5/2008 | Falco et al. |
| 2008/0144906 A1 | 6/2008 | Allred et al. |
| 2008/0161680 A1 | 7/2008 | von Jako et al. |
| 2008/0161682 A1 | 7/2008 | Kendrick et al. |
| 2008/0177203 A1 | 7/2008 | von Jako |
| 2008/0214922 A1 | 9/2008 | Hartmann et al. |
| 2008/0228068 A1 | 9/2008 | Viswanathan et al. |
| 2008/0228196 A1 | 9/2008 | Wang et al. |
| 2008/0235052 A1 | 9/2008 | Node-Langlois et al. |
| 2008/0269596 A1 | 10/2008 | Revie et al. |
| 2008/0287771 A1 | 11/2008 | Anderson |
| 2008/0287781 A1 | 11/2008 | Revie et al. |
| 2008/0300477 A1 | 12/2008 | Lloyd et al. |
| 2008/0300478 A1 | 12/2008 | Zuhars et al. |
| 2008/0302950 A1 | 12/2008 | Park et al. |
| 2008/0306490 A1 | 12/2008 | Lakin et al. |
| 2008/0319311 A1 | 12/2008 | Hamadeh |
| 2009/0012509 A1 | 1/2009 | Csavoy et al. |
| 2009/0030428 A1 | 1/2009 | Omori et al. |
| 2009/0080737 A1 | 3/2009 | Battle et al. |
| 2009/0128618 A1* | 5/2009 | Fahn ................. H04N 23/58 348/E7.001 |
| 2009/0185655 A1 | 7/2009 | Koken et al. |
| 2009/0198121 A1 | 8/2009 | Hoheisel |
| 2009/0216113 A1 | 8/2009 | Meier et al. |
| 2009/0228019 A1 | 9/2009 | Gross et al. |
| 2009/0259123 A1 | 10/2009 | Navab et al. |
| 2009/0259230 A1 | 10/2009 | Khadem et al. |
| 2009/0264899 A1 | 10/2009 | Appenrodt et al. |
| 2009/0281417 A1 | 11/2009 | Hartmann et al. |
| 2010/0022874 A1 | 1/2010 | Wang et al. |
| 2010/0039506 A1 | 2/2010 | Sarvestani et al. |
| 2010/0125286 A1 | 5/2010 | Wang et al. |
| 2010/0130986 A1 | 5/2010 | Mailloux et al. |
| 2010/0228117 A1 | 9/2010 | Hartmann |
| 2010/0228265 A1 | 9/2010 | Prisco |
| 2010/0249571 A1 | 9/2010 | Jensen et al. |
| 2010/0274120 A1 | 10/2010 | Heuscher |
| 2010/0280363 A1 | 11/2010 | Skarda et al. |
| 2010/0331858 A1 | 12/2010 | Simaan et al. |
| 2011/0022229 A1 | 1/2011 | Jang et al. |
| 2011/0077504 A1 | 3/2011 | Fischer et al. |
| 2011/0098553 A1 | 4/2011 | Robbins et al. |
| 2011/0137152 A1 | 6/2011 | Li |
| 2011/0213384 A1 | 9/2011 | Jeong |
| 2011/0224684 A1 | 9/2011 | Larkin et al. |
| 2011/0224685 A1 | 9/2011 | Larkin et al. |
| 2011/0224686 A1 | 9/2011 | Larkin et al. |
| 2011/0224687 A1 | 9/2011 | Larkin et al. |
| 2011/0224688 A1 | 9/2011 | Larkin et al. |
| 2011/0224689 A1 | 9/2011 | Larkin et al. |
| 2011/0224825 A1 | 9/2011 | Larkin et al. |
| 2011/0230967 A1 | 9/2011 | O'Halloran et al. |
| 2011/0238080 A1 | 9/2011 | Ranjit et al. |
| 2011/0276058 A1 | 11/2011 | Choi et al. |
| 2011/0282189 A1 | 11/2011 | Graumann |
| 2011/0286573 A1 | 11/2011 | Schretter et al. |
| 2011/0295062 A1 | 12/2011 | Gratacos Solsona et al. |
| 2011/0295370 A1 | 12/2011 | Suh et al. |
| 2011/0306986 A1 | 12/2011 | Lee et al. |
| 2012/0035507 A1 | 2/2012 | George et al. |
| 2012/0046668 A1 | 2/2012 | Gantes |
| 2012/0051498 A1 | 3/2012 | Koishi |
| 2012/0053597 A1 | 3/2012 | Anvari et al. |
| 2012/0059248 A1 | 3/2012 | Holsing et al. |
| 2012/0071753 A1 | 3/2012 | Hunter et al. |
| 2012/0108954 A1 | 5/2012 | Schulhauser et al. |
| 2012/0136372 A1 | 5/2012 | Amat Girbau et al. |
| 2012/0143084 A1 | 6/2012 | Shoham |
| 2012/0184839 A1 | 7/2012 | Woerlein |
| 2012/0197182 A1 | 8/2012 | Millman et al. |
| 2012/0226145 A1 | 9/2012 | Chang et al. |
| 2012/0235909 A1 | 9/2012 | Birkenbach et al. |
| 2012/0245596 A1 | 9/2012 | Meenink |
| 2012/0253332 A1 | 10/2012 | Moll |
| 2012/0253360 A1 | 10/2012 | White et al. |
| 2012/0256092 A1 | 10/2012 | Zingerman |
| 2012/0294498 A1 | 11/2012 | Popovic |
| 2012/0296203 A1 | 11/2012 | Hartmann et al. |
| 2013/0006267 A1 | 1/2013 | Odermatt et al. |
| 2013/0016889 A1 | 1/2013 | Myronenko et al. |
| 2013/0030571 A1 | 1/2013 | Ruiz Morales et al. |
| 2013/0035583 A1 | 2/2013 | Park et al. |
| 2013/0060146 A1 | 3/2013 | Yang et al. |
| 2013/0060337 A1 | 3/2013 | Petersheim et al. |
| 2013/0094742 A1 | 4/2013 | Feilkas |
| 2013/0096574 A1 | 4/2013 | Kang et al. |
| 2013/0113791 A1 | 5/2013 | Isaacs et al. |
| 2013/0116706 A1 | 5/2013 | Lee et al. |
| 2013/0131695 A1 | 5/2013 | Scarfogliero et al. |
| 2013/0144307 A1 | 6/2013 | Jeong et al. |
| 2013/0158542 A1 | 6/2013 | Manzo et al. |
| 2013/0165937 A1 | 6/2013 | Patwardhan |
| 2013/0178867 A1 | 7/2013 | Farritor et al. |
| 2013/0178868 A1 | 7/2013 | Roh |
| 2013/0178870 A1 | 7/2013 | Schena |
| 2013/0204271 A1 | 8/2013 | Brisson et al. |
| 2013/0211419 A1 | 8/2013 | Jensen |
| 2013/0211420 A1 | 8/2013 | Jensen |
| 2013/0218142 A1 | 8/2013 | Tuma et al. |
| 2013/0223702 A1 | 8/2013 | Holsing et al. |
| 2013/0225942 A1 | 8/2013 | Holsing et al. |
| 2013/0225943 A1 | 8/2013 | Holsing et al. |
| 2013/0231556 A1 | 9/2013 | Holsing et al. |
| 2013/0237995 A1 | 9/2013 | Lee et al. |
| 2013/0245375 A1 | 9/2013 | DiMaio et al. |
| 2013/0261640 A1 | 10/2013 | Kim et al. |

(56) References Cited

U.S. PATENT DOCUMENTS

| | | |
|---|---|---|
| 2013/0272488 A1 | 10/2013 | Bailey et al. |
| 2013/0272489 A1 | 10/2013 | Dickman et al. |
| 2013/0274761 A1 | 10/2013 | Devengenzo et al. |
| 2013/0281821 A1 | 10/2013 | Liu et al. |
| 2013/0296884 A1 | 11/2013 | Taylor et al. |
| 2013/0303887 A1 | 11/2013 | Holsing et al. |
| 2013/0307955 A1 | 11/2013 | Deitz et al. |
| 2013/0317521 A1 | 11/2013 | Choi et al. |
| 2013/0325033 A1 | 12/2013 | Schena et al. |
| 2013/0325035 A1 | 12/2013 | Hauck et al. |
| 2013/0331686 A1 | 12/2013 | Freysinger et al. |
| 2013/0331858 A1 | 12/2013 | Devengenzo et al. |
| 2013/0331861 A1 | 12/2013 | Yoon |
| 2013/0342578 A1 | 12/2013 | Isaacs |
| 2013/0345717 A1 | 12/2013 | Markvicka et al. |
| 2013/0345757 A1 | 12/2013 | Stad |
| 2014/0001235 A1 | 1/2014 | Shelton, IV |
| 2014/0012131 A1 | 1/2014 | Heruth et al. |
| 2014/0031664 A1 | 1/2014 | Kang et al. |
| 2014/0046128 A1 | 2/2014 | Lee et al. |
| 2014/0046132 A1 | 2/2014 | Hoeg et al. |
| 2014/0046340 A1 | 2/2014 | Wilson et al. |
| 2014/0049629 A1 | 2/2014 | Siewerdsen et al. |
| 2014/0058406 A1 | 2/2014 | Tsekos |
| 2014/0073914 A1 | 3/2014 | Lavallee et al. |
| 2014/0080086 A1 | 3/2014 | Chen |
| 2014/0081128 A1 | 3/2014 | Verard et al. |
| 2014/0088612 A1 | 3/2014 | Bartol et al. |
| 2014/0094694 A1 | 4/2014 | Moctezuma de la Barrera |
| 2014/0094851 A1 | 4/2014 | Gordon |
| 2014/0096369 A1 | 4/2014 | Matsumoto et al. |
| 2014/0100587 A1 | 4/2014 | Farritor et al. |
| 2014/0121676 A1 | 5/2014 | Kostrzewski et al. |
| 2014/0128882 A1 | 5/2014 | Kwak et al. |
| 2014/0135796 A1 | 5/2014 | Simon et al. |
| 2014/0142591 A1 | 5/2014 | Alvarez et al. |
| 2014/0142592 A1 | 5/2014 | Moon et al. |
| 2014/0148692 A1 | 5/2014 | Hartmann et al. |
| 2014/0163581 A1 | 6/2014 | Devengenzo et al. |
| 2014/0171781 A1 | 6/2014 | Stiles |
| 2014/0171900 A1 | 6/2014 | Stiles |
| 2014/0171965 A1 | 6/2014 | Loh et al. |
| 2014/0180308 A1 | 6/2014 | von Grunberg |
| 2014/0180309 A1 | 6/2014 | Seeber et al. |
| 2014/0187915 A1 | 7/2014 | Yaroshenko et al. |
| 2014/0188132 A1 | 7/2014 | Kang |
| 2014/0194699 A1 | 7/2014 | Roh et al. |
| 2014/0130810 A1 | 8/2014 | Azizian et al. |
| 2014/0221819 A1 | 8/2014 | Sarment |
| 2014/0222023 A1 | 8/2014 | Kim et al. |
| 2014/0228631 A1 | 8/2014 | Kwak et al. |
| 2014/0234804 A1 | 8/2014 | Huang et al. |
| 2014/0257328 A1 | 9/2014 | Kim et al. |
| 2014/0257329 A1 | 9/2014 | Jang et al. |
| 2014/0257330 A1 | 9/2014 | Choi et al. |
| 2014/0275760 A1 | 9/2014 | Lee et al. |
| 2014/0275985 A1 | 9/2014 | Walker et al. |
| 2014/0276931 A1 | 9/2014 | Parihar et al. |
| 2014/0276940 A1 | 9/2014 | Seo |
| 2014/0276944 A1 | 9/2014 | Farritor et al. |
| 2014/0288413 A1 | 9/2014 | Hwang et al. |
| 2014/0299648 A1 | 10/2014 | Shelton, IV et al. |
| 2014/0303434 A1 | 10/2014 | Farritor et al. |
| 2014/0303643 A1 | 10/2014 | Ha et al. |
| 2014/0305995 A1 | 10/2014 | Shelton, IV et al. |
| 2014/0309659 A1 | 10/2014 | Roh et al. |
| 2014/0316436 A1 | 10/2014 | Bar et al. |
| 2014/0323803 A1 | 10/2014 | Hoffman et al. |
| 2014/0324070 A1 | 10/2014 | Min et al. |
| 2014/0330288 A1 | 11/2014 | Date et al. |
| 2014/0364720 A1 | 12/2014 | Darrow et al. |
| 2014/0371577 A1 | 12/2014 | Maillet et al. |
| 2015/0039034 A1 | 2/2015 | Frankel et al. |
| 2015/0085970 A1 | 3/2015 | Bouhnik et al. |
| 2015/0146847 A1 | 5/2015 | Liu |
| 2015/0150524 A1 | 6/2015 | Yorkston et al. |
| 2015/0196261 A1 | 7/2015 | Funk |
| 2015/0213633 A1 | 7/2015 | Chang et al. |
| 2015/0335480 A1 | 11/2015 | Alvarez et al. |
| 2015/0342647 A1 | 12/2015 | Frankel et al. |
| 2016/0005194 A1 | 1/2016 | Schretter et al. |
| 2016/0166329 A1 | 6/2016 | Langan et al. |
| 2016/0235480 A1 | 8/2016 | Scholl et al. |
| 2016/0249990 A1 | 9/2016 | Glozman et al. |
| 2016/0302871 A1 | 10/2016 | Gregerson et al. |
| 2016/0320322 A1 | 11/2016 | Suzuki |
| 2016/0331335 A1 | 11/2016 | Gregerson et al. |
| 2017/0135770 A1 | 5/2017 | Scholl et al. |
| 2017/0143284 A1 | 5/2017 | Sehnert et al. |
| 2017/0143426 A1 | 5/2017 | Isaacs et al. |
| 2017/0156816 A1 | 6/2017 | Ibrahim |
| 2017/0202629 A1 | 7/2017 | Maillet et al. |
| 2017/0212723 A1 | 7/2017 | Atarot et al. |
| 2017/0215825 A1 | 8/2017 | Johnson et al. |
| 2017/0215826 A1 | 8/2017 | Johnson et al. |
| 2017/0215827 A1 | 8/2017 | Johnson et al. |
| 2017/0231710 A1 | 8/2017 | Scholl et al. |
| 2017/0258426 A1 | 9/2017 | Risher-Kelly et al. |
| 2017/0273748 A1 | 9/2017 | Hourtash et al. |
| 2017/0296277 A1 | 10/2017 | Hourtash et al. |
| 2017/0360493 A1 | 12/2017 | Zucher et al. |
| 2022/0110682 A1* | 4/2022 | Tseng ................... G06T 19/20 |
| 2022/0215539 A1* | 7/2022 | Proksch ................ A61B 34/30 |

* cited by examiner

EXTENDED REALITY SYSTEMS WITH THREE-DIMENSIONAL VISUALIZATIONS OF MEDICAL IMAGE SCAN SLICES

CROSS REFERENCE TO RELATED APPLICATIONS

This application is a continuation patent application of U.S. patent application Ser. No. 17/539,796 filed on Dec. 1, 2021, which is incorporated in its entirety herein.

FIELD

The present disclosure relates to computer systems for planning surgical operations and computer assisted navigation of equipment and operators during surgery.

BACKGROUND

Surgical operating rooms can contain a diverse range of medical equipment, which can include computer assisted surgical navigation systems, surgical robot systems, medical imaging devices (e.g., computerized tomography (CT) scanners, magnetic resonance imaging scanners, fluoroscopy imaging, etc.), neuromonitoring equipment, patient monitors, microscopes, anesthesia equipment, etc.

A computer assisted surgical navigation system can provide a surgeon with computerized visualization of the present pose of a surgical tool relative to medical images of a patient's anatomy. Camera tracking systems for computer assisted surgical navigation typically use a set of cameras to track a tool reference array on a surgical tool which is being positioned by a surgeon during surgery relative to a patient reference array attached to a patient. The reference array, also referred to as a dynamic reference array (DRA) or dynamic reference base (DRB), allows the camera tracking system to determine a pose of the surgical tool relative to anatomical structure within a medical image and relative to the patient. The surgeon can thereby use real-time visual feedback of the determined pose(s) to navigate the surgical tool during a surgical procedure on the patient.

Many surgical workflows using computer assisted surgical navigation systems require medical image scans, such as CT scans or magnetic resonance imaging scans, during operation and/or registration procedures. Perpendicular scan slices (axial, sagittal, and coronal) are used to enable operators to visualize the patient's anatomy alongside the relative poses of surgical instruments. Projections of the three-dimensional (3D) scan can also be shown. When showing 3D models of a patient's anatomy alongside two-dimensional (2D) slices, it can be challenging for an operator to know how the 3D model and the patient anatomy relates geometrically to the 2D slices.

SUMMARY

Some embodiments of the present disclosure are directed to providing a navigated surgery system that enables a user wearing an extended reality (XR) headset to visualize how a displayed 2D medical image slice of anatomical structure of a patient relates geometrically to a displayed 3D graphical model of anatomical structure.

In some embodiments, a navigated surgery system includes at least one processor that is operative to obtain a first 2D medical image slice of anatomical structure of a patient. The operations obtain a 3D graphical model of anatomical structure. The operations determine a first pose of a first virtual cross-sectional plane extending through the 3D graphical model of the anatomical structure that corresponds to the anatomical structure of the first 2D medical image slice. The operations control the XR headset to display the first 2D medical image slice of the anatomical structure of the patient, display the 3D graphical model of the anatomical structure, and display a first graphical object oriented with the first pose relative to the 3D graphical model of the anatomical structure.

Other navigated surgery systems and corresponding methods and computer program products according to embodiments of the inventive subject matter will be or become apparent to one with skill in the art upon review of the following drawings and detailed description. It is intended that all such additional navigated surgery systems, methods. and computer program products be included within this description, be within the scope of the present inventive subject matter, and be protected by the accompanying claims. Moreover, it is intended that all embodiments disclosed herein can be implemented separately or combined in any way and/or combination.

DESCRIPTION OF THE DRAWINGS

Aspects of the present disclosure are illustrated by way of example and are not limited by the accompanying drawings. In the drawings.

DETAILED DESCRIPTION

Figure 1:
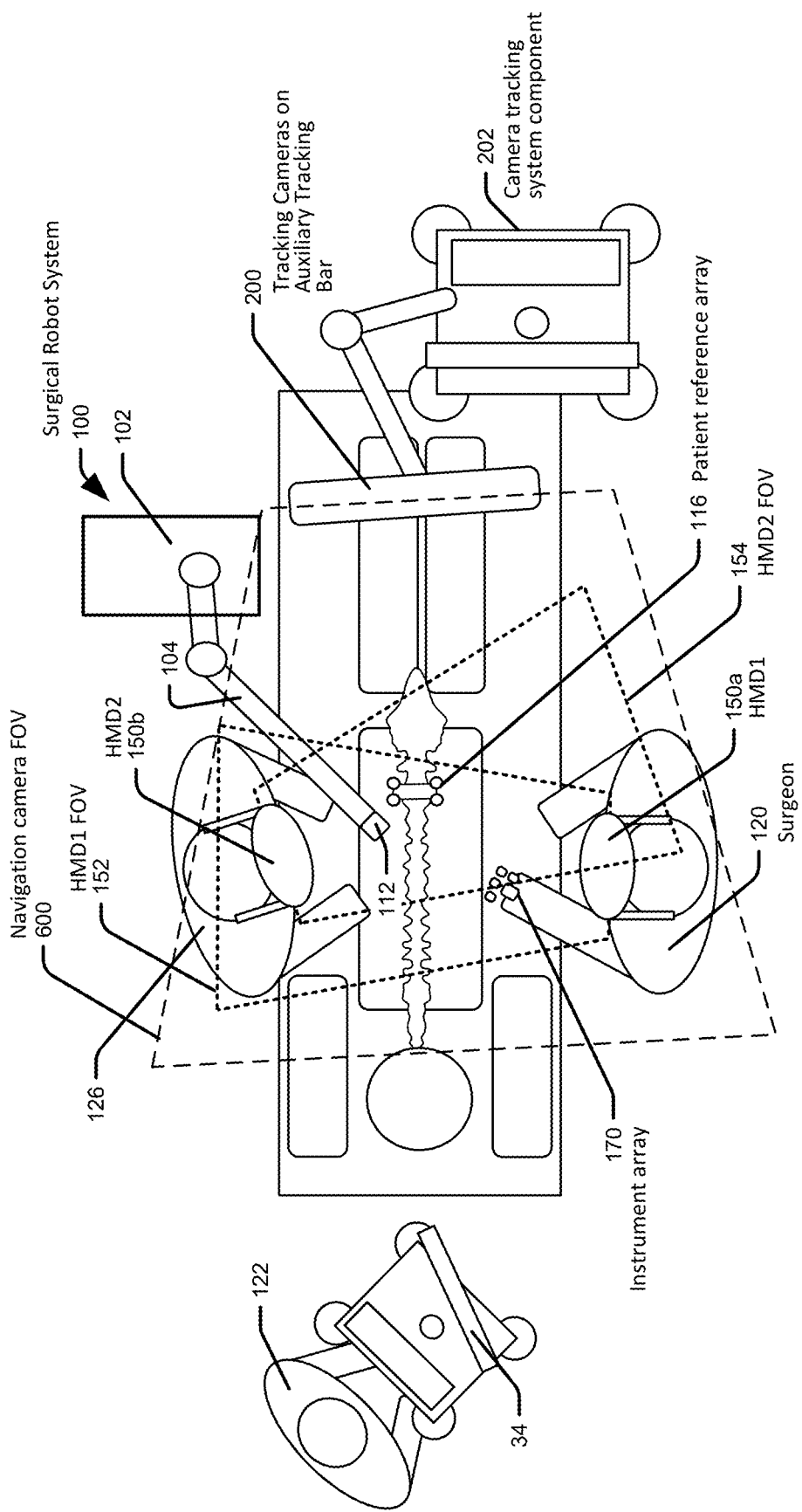
FIG. 1 is an overhead view of a personnel wearing extended reality (XR) headsets during a surgical procedure in a surgical room that includes a camera tracking system for navigated surgery and a surgical robot system for robotic assistance, in accordance with some embodiments.

It is to be understood that the present disclosure is not limited in its application to the details of construction and the arrangement of components set forth in the description herein or illustrated in the drawings. The teachings of the present disclosure may be used and practiced in other embodiments and practiced or carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

The following discussion is presented to enable a person skilled in the art to make and use embodiments of the present disclosure. Various modifications to the illustrated embodiments will be readily apparent to those skilled in the art, and the principles herein can be applied to other embodiments and applications without departing from embodiments of the present disclosure. Thus, the embodiments are not intended to be limited to embodiments shown, but are to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of the embodiments. Skilled artisans will recognize the examples provided herein have many useful alternatives and fall within the scope of the embodiments.

Figure 2:
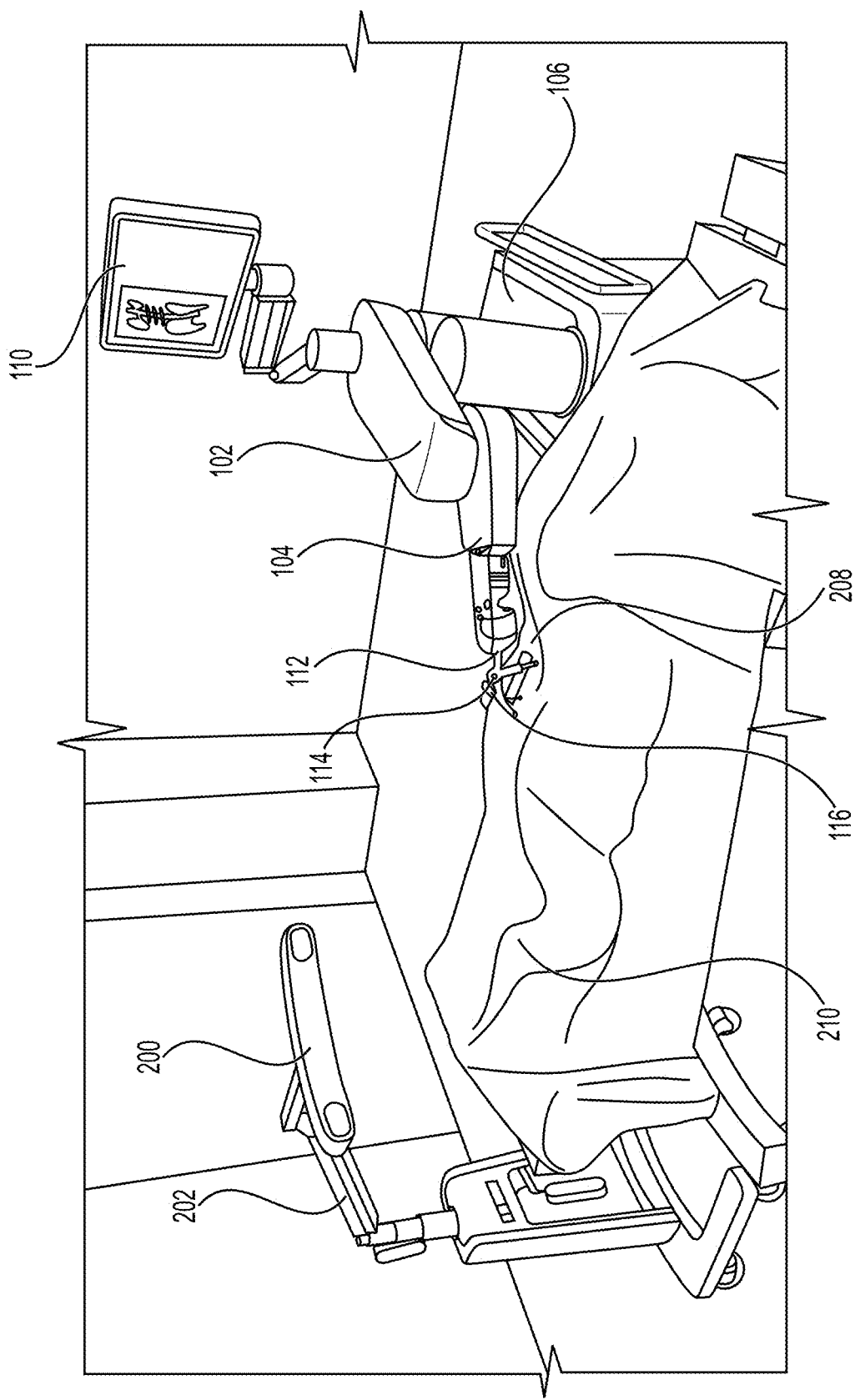
FIG. 2 illustrates the navigated surgery camera tracking system and the surgical robot system positioned relative to a patient, according to some embodiments.
Figure 3:
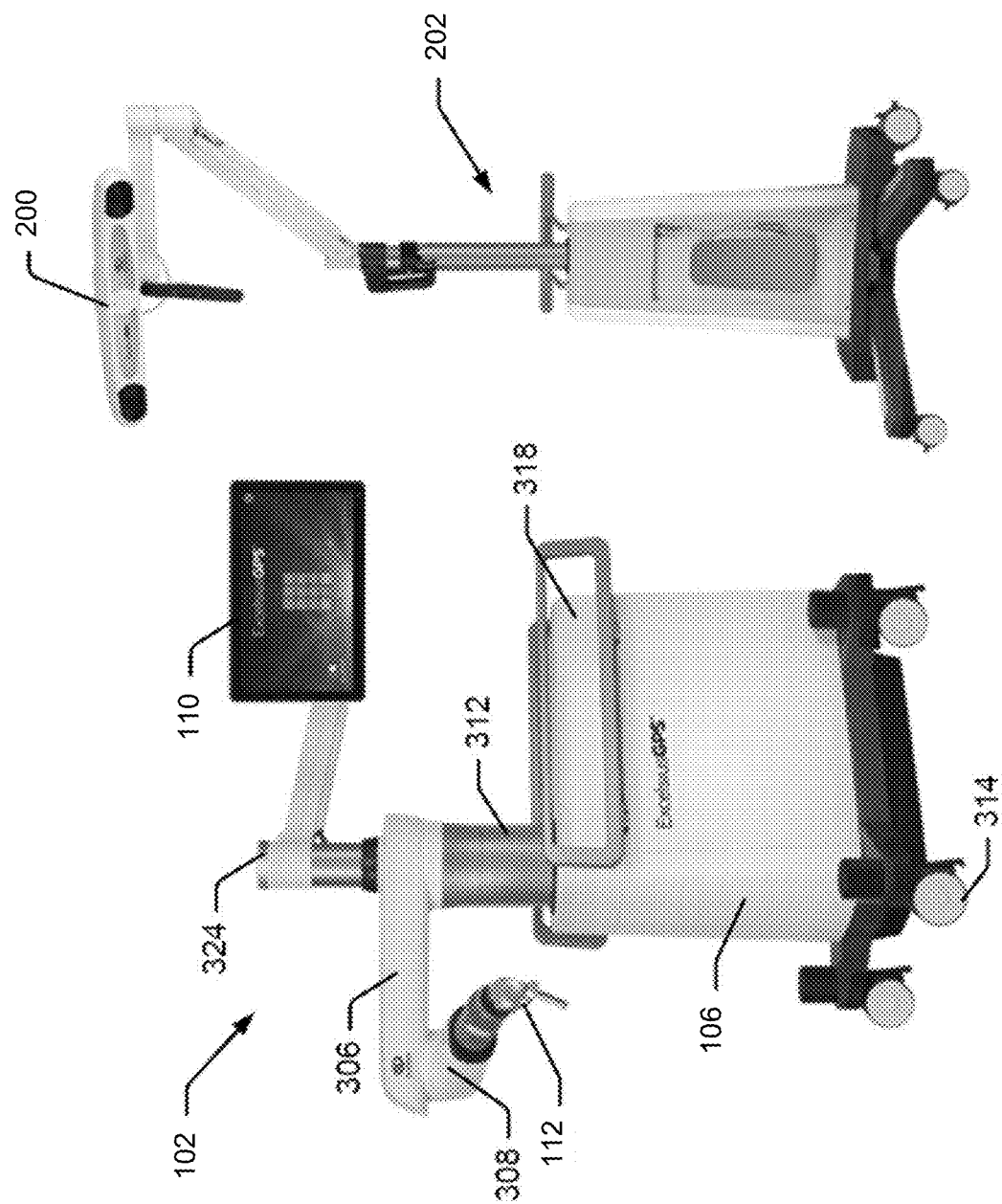
FIG. 3 illustrates a navigated surgery camera tracking system and a surgical robot system configured according to some embodiments.

Turning now to the drawing, FIG. 1 is an overhead view of personnel wearing extended reality (XR) headsets 150a and 150b during a surgical procedure in a surgical room that includes a camera tracking system 200 for navigated surgery and a surgical robot system 100 for robotic assistance, in accordance with some embodiments. FIG. 2 illustrates the navigated surgery camera tracking system 202 and the surgical robot system 100 positioned relative to a patient, according to some embodiments. FIG. 3 illustrates the navigated surgery camera tracking system 202 and the surgical robot system 100 configured according to some embodiments.

An XR headset may be configured to augment a real-world scene with computer generated XR images. The XR headset may be configured to provide an augmented reality (AR) viewing environment by displaying the computer generated XR images on a see-through display screen that allows light from the real-world scene to pass therethrough for combined viewing by the user. Alternatively, the XR headset may be configured to provide a virtual reality (VR) viewing environment by preventing or substantially preventing light from the real-world scene from being directly viewed by the user while the user is viewing the computer generated AR images on a display screen. An XR headset can be configured to provide both AR and VR viewing environments. Thus, the term XR headset can referred to as an AR headset or a VR headset.

Referring to FIGS. 1-3, the surgical robot system 100 may include, for example, a surgical robot 102, one or more robot arms 104, a display 110, an end-effector 112, for example, including a guide tube 114, and an end effector reference array which can include one or more tracking markers. The surgical robot system 100 may include a patient reference array 116 with a plurality of tracking markers, which is adapted to be secured directly to the patient 210 (e.g., to a bone of the patient 210). Another reference array 170 is attached or formed on an instrument, surgical tool, surgical implant device, etc. The surgical robot system 100 may also utilize a tracking camera 200, for example, positioned on the camera tracking system 202. The camera tracking system 202 can have any suitable configuration to move, orient, and support the tracking camera 200 in a desired position, and may contain a computer operable to track pose of reference arrays.

The tracking camera 200 may include any suitable camera or cameras, such as one or more infrared cameras (e.g., bifocal or stereophotogrammetric cameras), able to identify, for example, active and passive tracking markers for various reference arrays attached as the patient 210 (patient reference array), end effector 112 (end effector reference array), extended reality (XR) headset(s) 150a-150b worn by a surgeon 120 and/or a surgical assistant 126, etc. in a given measurement volume viewable from the perspective of the tracking camera 200. The tracking camera 200 may track markers 170 attached to a surgical tool, implant, or instrument manipulated by a user. The tracking camera 200 may scan the given measurement volume and detect the light that is emitted or reflected from the reference arrays in order to identify and determine poses of the reference arrays in three-dimensions. For example, active reference arrays may include infrared-emitting markers that are activated by an electrical signal (e.g., infrared light emitting diodes (LEDs)), and passive reference arrays may include retro-reflective markers that reflect infrared light (e.g., they reflect incoming IR radiation into the direction of the incoming light), for example, emitted by illuminators on the tracking camera 200 or other suitable device.

The XR headsets 150a and 150b (also referred to as an XR headset 150) may each include tracking cameras that can track poses of reference arrays within their camera field-of-views (FOVs) 152 and 154, respectively. Accordingly, as illustrated in FIG. 1, the poses of reference arrays attached to various objects can be tracked while in the FOVs 152 and 154 of the XR headsets 150a and 150b and/or a FOV 600 of the tracking cameras 200.

FIGS. 1 and 2 illustrate a potential configuration for the placement of the camera tracking system 202 and the surgical robot system 100 in an operating room environment. Computer-aided navigated surgery can be provided by the camera tracking system controlling the XR headsets 150a and 150b to display surgical procedure navigation information. The surgical robot system 100 in optional during computer-aided navigated surgery.

The camera tracking system 202 may use tracking information and other information from multiple XR headsets 150a and 150b such as inertial tracking information and optical tracking information as well as (optional) microphone information. The XR headsets 150a and 150b operate to display visual information and play-out audio information to the wearer. This information can be from local sources (e.g., the surgical robot 102 and/or other medical), remote sources (e.g., patient medical image server), and/or other electronic equipment. The XR headsets 150a and 150b track apparatus such as instruments, patient references and end effectors in 6 degrees-of-freedom (6DOF), and may track the hands of the wearer. The XR headsets 150a and 150b may also operate to track hand poses and gestures to enable gesture based interactions with "virtual" buttons and interfaces displayed through the XR headsets 150a and 150b and can also interpret hand or finger pointing or gesturing as various defined commands. Additionally, the XR headsets 150a and 150b may have a 1-10× magnification digital color camera sensor called a digital loupe.

An "outside-in" machine vision navigation bar (tracking cameras 200) tracks instruments and may include a color camera. The machine vision navigation bar generally has a more stable view of the environment because it does not move as often or as quickly as the XR headsets 150a and 150b tend to move while positioned on wearers' heads. The patient reference array 116 is generally rigidly attached to the patient with stable pitch and roll relative to gravity. This local rigid patient reference 116 can serve as a common reference for reference frames relative to other tracked arrays, such as a reference array on the end effector 112, instrument reference array 170, and reference arrays on the XR headsets 150a and 150b.

In some embodiments, one or more of the XR headsets 150a and 150b are minimalistic XR headsets that display local or remote information but include fewer sensors and are therefore more lightweight.

When present, the surgical robot system (also "robot") 102 may be positioned near or next to patient 210. Although depicted near the head of the patient 210, it will be appreciated that the robot 102 can be positioned at any suitable location near the patient 210 depending on the area of the patient 210 undergoing a surgical procedure. The tracking camera 200 may be separated from the robot system 100 and positioned at the foot of patient 210. This location allows the tracking camera 200 to have a direct visual line of sight to the surgical field 208. Again, it is contemplated that the tracking camera 200 may be located at any suitable position having line of sight to the surgical field 208. In the configuration shown, the surgeon 120 may be positioned across from the robot 102, but is still able to manipulate the end-effector 112 and the display 110. A surgical assistant 126 may be positioned across from the surgeon 120 again with access to both the end-effector 112 and the display 110. If desired, the locations of the surgeon 120 and the assistant 126 may be reversed. The traditional areas for the anesthesiologist 122 and the nurse or scrub tech 124 remain unimpeded by the locations of the robot 102 and camera 200. The anesthesiologist 122 can operate anesthesia equipment which can include a display 34.

With respect to the other components of the robot 102, the display 110 can be attached to the surgical robot 102 and in other example embodiments, display 110 can be detached from surgical robot 102, either within a surgical room with the surgical robot 102, or in a remote location. End-effector 112 may be coupled to the robot arm 104 and controlled by at least one motor. In example embodiments, end-effector 112 can comprise a guide tube 114, which is able to receive and orient a surgical instrument, tool, or implant 608 used to perform a surgical procedure on the patient 210.

As used herein, the term "end-effector" is used interchangeably with the terms "end-effectuator" and "effectuator element." The term "instrument" is used in a non-limiting manner and can be used interchangeably with "tool" and "implant" to generally refer to any type of device that can be used during a surgical procedure in accordance with embodiments disclosed herein. Example instruments, tools, and implants include, without limitation, drills, screwdrivers, saws, dilators, retractors, probes, implant inserters, and implant devices such as a screws, spacers, interbody fusion devices, plates, rods, etc. Although generally shown with a guide tube 114, it will be appreciated that the end-effector 112 may be replaced with any suitable instrumentation suitable for use in surgery. In some embodiments, end-effector 112 can comprise any known structure for effecting the movement of the surgical instrument 608 in a desired manner.

The surgical robot 102 is operable to control the translation and orientation of the end-effector 112. The robot 102 is operable to move end-effector 112 under computer control along x-, y-, and z-axes, for example. The end-effector 112 can be configured for selective rotation about one or more of the x-, y-, and z-axis, and a Z Frame axis (such that one or more of the Euler Angles (e.g., roll, pitch, and/or yaw) associated with end-effector 112 can be selectively computer controlled). In some example embodiments, selective control of the translation and orientation of end-effector 112 can permit performance of medical procedures with significantly improved accuracy compared to conventional robots that utilize, for example, a six degree of freedom robot arm comprising only rotational axes. For example, the surgical robot system 100 may be used to operate on patient 210, and robot arm 104 can be positioned above the body of patient 210, with end-effector 112 selectively angled relative to the z-axis toward the body of patient 210.

In some example embodiments, the XR headsets 150a and 150b can be controlled to dynamically display an updated graphical indication of the pose of the surgical instrument so that the user can be aware of the pose of the surgical instrument at all times during the procedure.

As used herein, the term "pose" refers to the position and/or the rotational angle of one object (e.g., dynamic reference array, end-effector, surgical instrument, anatomical structure, etc.) relative to another object and/or to a defined coordinate system. A pose may therefore be defined based on only the multidimensional position of one object relative to another object and/or relative to a defined coordinate system, based on only the multidimensional rotational angles of the object relative to another object and/or to a defined coordinate system, or based on a combination of the multidimensional position and the multidimensional rotational angles. The term "pose" therefore is used to refer to position, rotational angle, or combination thereof.

In some further embodiments, surgical robot 102 can be configured to correct the path of a surgical instrument guided by the robot arm 104 if the surgical instrument strays from the selected, preplanned trajectory. In some example embodiments, surgical robot 102 can be configured to permit stoppage, modification, and/or manual control of the movement of end-effector 112 and/or the surgical instrument. Thus, in use, in example embodiments, a surgeon or other user can operate the system 100, and has the option to stop, modify, or manually control the autonomous movement of end-effector 112 and/or the surgical instrument.

Reference arrays can be formed on or connected to robot arm 104, end-effector 112, patient 210, and/or the surgical instrument to track poses in 6 degree-of-freedom (e.g., position along 3 orthogonal axes and rotation about the axes). In example embodiments, a reference array including a plurality of tracking markers can be provided thereon (e.g., formed-on or connected-to) to an outer surface of the robot 102, such as on robot 102, on robot arm 104, and/or on the end-effector 112. A patient reference array including one or more tracking markers can further be provided on the patient 210 (e.g., formed-on or connected-to). An instrument reference array including one or more tracking markers can be provided on surgical instruments (e.g., a screwdriver, dilator, implant inserter, or the like). The reference arrays enable each of the marked objects (e.g., the end-effector 112, the patient 210, and the surgical instruments) to be tracked by the tracking camera 200, and the tracked poses can be used to provide navigation guidance to a surgical procedure and/or used to control movement of the surgical robot 102 for guiding the end-effector 112 and/or an instrument.

Referring to FIG. 3 the surgical robot system 100 includes the surgical robot 102 including a display 110, upper arm 306, lower arm 308, end-effector 112, vertical column 312, casters 314, tablet drawer 318, and ring 324 which uses lights to indicate statuses and other information. Cabinet 106 may house certain components of surgical robot system 100 including but not limited to a battery, a power distribution module, a platform interface board module, and a computer. The tracking camera 200 is supported by the camera tracking system 202.

Figure 4A:
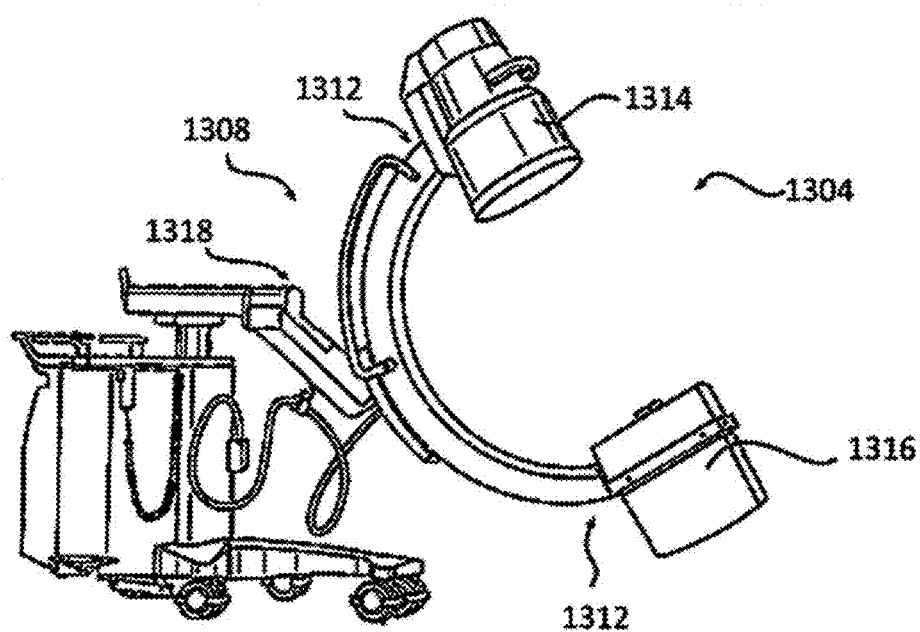
FIGS. 4A-4B respectively illustrate a C-arm image device and an O-arm imaging device in accordance with some embodiments.
Figure 4B:
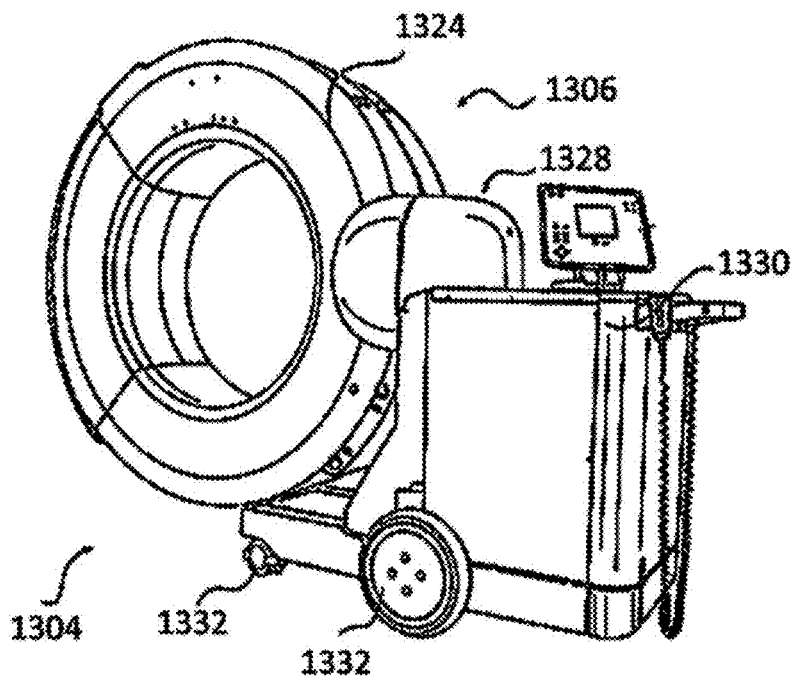

FIGS. 4A and 4B illustrate medical imaging systems 1304 that may be used in conjunction with the camera tracking system 202 for navigated surgery, to acquire pre-operative, intra-operative, post-operative, and/or real-time image data of patient 210. Any necessary anatomical structure may be imaged for any appropriate procedure using the imaging system 1304. The imaging system 1304 may be any imaging device such as a C-arm computerized tomography (CT) scan device 1308, an O-arm CT scan device 1306, a fluoroscopy imaging device, a magnetic resonance imaging scanner, etc. It may be desirable to take x-rays of patient 210 from a number of different positions, without the need for frequent manual repositioning of patient 210 which may be required in an x-ray system. As illustrated in FIG. 4A, the imaging system 1304 may be in the form of a C-arm 1308 that includes an elongated C-shaped member terminating in opposing distal ends 1312 of the "C" shape. C-shaped member 1130 may further comprise an x-ray source 1314 and an image receptor 1316. The space within C-arm 1308 of the arm may provide room for the physician to attend to the patient substantially free of interference from x-ray support structure 1318. As illustrated in FIG. 4B, the imaging system 1304 may include an O-arm imaging device 1306 having a gantry housing 1324 attached to a support structure imaging device support structure 1328, such as a wheeled mobile cart 1330 with wheels 1332, which may enclose an image capturing portion, not illustrated. The image capturing portion may include an x-ray source and/or emission portion and an x-ray receiving and/or image receiving portion, which may be disposed about one hundred and eighty degrees from each other and mounted on a rotor (not illustrated) relative to a track of the image capturing portion. The image capturing portion may be operable to rotate three hundred and sixty degrees during image acquisition. The image capturing portion may rotate around a central point and/or axis, allowing image data of patient 210 to be acquired from multiple directions or in multiple planes. Although certain imaging systems 1304 are exemplified herein, it will be appreciated that any suitable imaging system may be selected by one of ordinary skill in the art.

XR Headset View of 2D Medical Image Slices of Patient Anatomical Structure and 3D Graphical Model of Anatomical Structure As was explained above, in traditional computer-assisted navigated surgeries, perpendicular 2D scan slices, such as axial, sagittal, and/or coronal views, of patient anatomical structure are used to visualize the patient's anatomy alongside the relative poses of surgical instruments. In accordance with various embodiments of the present disclosure, an XR headset is controlled to display one or more 2D scan slices of patient anatomy along with a 3D graphical model of anatomy. The 3D graphical model may be generated from a 3D scan of the patient, e.g., by a CT scan device, and/or may be generated based on a baseline model of anatomy which isn't necessarily formed from a scan of the patient.

When displaying the 3D graphical model concurrently with the one or more 2D scan slices through the XR headset, without further computer-aided assistance it is anticipated that it can be difficult for a user to understand how the 3D graphical model of anatomical structure geometrically relates to the anatomical structure captured in the one or more 2D scan slices. Various embodiments of the present disclosure are directed to providing a navigated surgery system that enables a user wearing the XR headset to visualize how the displayed 2D medical image slice of anatomical structure of a patient relates geometrically to a displayed 3D graphical model of anatomical structure.

As will be explained in further detail below, in some embodiments a navigated surgery system displays a graphical object through the XR headset that visually indicates a virtual cross-sectional plane extending through the 3D graphical model of the anatomical structure that corresponds to the anatomical structure of the first 2D medical image slice. Additional information, such as the orientation of the 2D scan slice and e.g., a current vertebral level may be displayed relative to the 3D graphical model.

Various embodiments display graphical objects that enable a user to visualize the pose of the cross-sectional plane(s) where the one or more 2D scan slice(s) geometrically correspond to visual "slice(s)" through the 3D graphical model. Although various embodiments are described in the context of orthopedic surgery, they are not limited to any type of surgery.

A navigation "plan" for navigated implanting of screws and/or other devices may be viewed based on navigation guidance information that is provided to the XR headsets 150a and 150b and/or 2D monitor for display.

Figure 5:
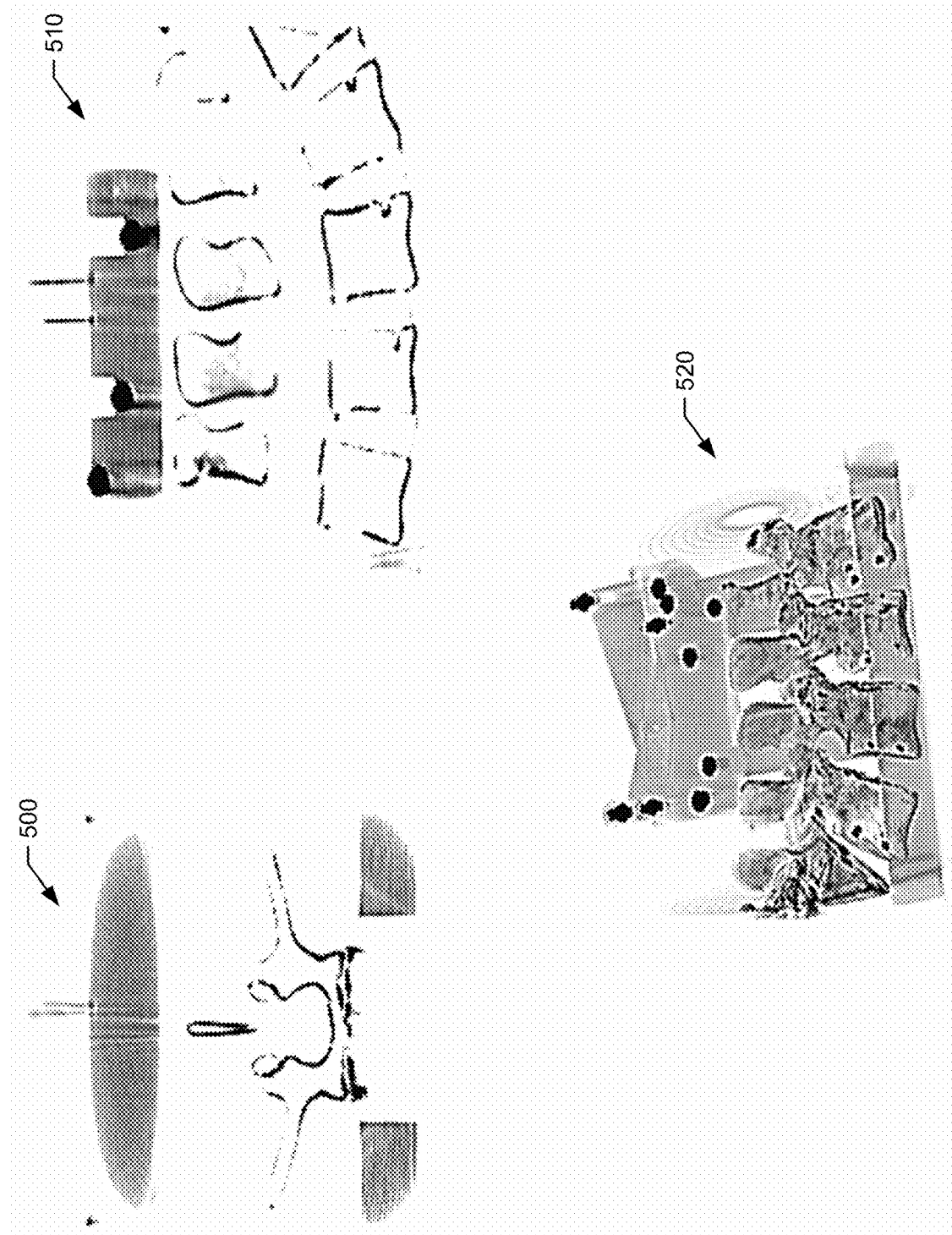
FIG. 5 illustrates an XR headset view of an axial 2D medical image slice of anatomical structure of a patient, a sagittal 2D medical image slice of the anatomical structure of the patient, and a 3D graphical model of anatomical structure, in accordance with some embodiments.

Basic Display of 2D Scan Slices and 3D Graphical Model Without Visualization of Geometric Correspondence FIG. 5 illustrates an XR headset view of an axial 2D medical image slice 500 of anatomical structure of a patient, a sagittal 2D medical image slice 510 of the anatomical structure of the patient, and a 3D graphical model 520 of anatomical structure, in accordance with some embodiments. The illustration of FIG. 5 does not include a computer-generated graphical object which is configured to visually assist the user (wearer of the XR headset) with determining how the 2D medical image slices 500 and 510 geometrically relate to the 3D graphical model 520. The 3D graphical model 520 may be registered to be displayed at or above the patient anatomy, when the patient is viewed through the XR headset, i.e., patient stabilized display. The axial 2D medical image slice 500 and the sagittal 2D medical image slice 510 may be registered to the user's head, i.e., head stabilized, so that they remain visible as the user looks around the surgical room. The XR headset may be further controlled to display other navigated surgery information, such as graphical representations of planned screw and interbody placement poses relative to the patient viewed through the XR headset and/or CAD graphical models which are displayed with poses that that updated to dynamically track sensed instrument poses.

Figure 6:
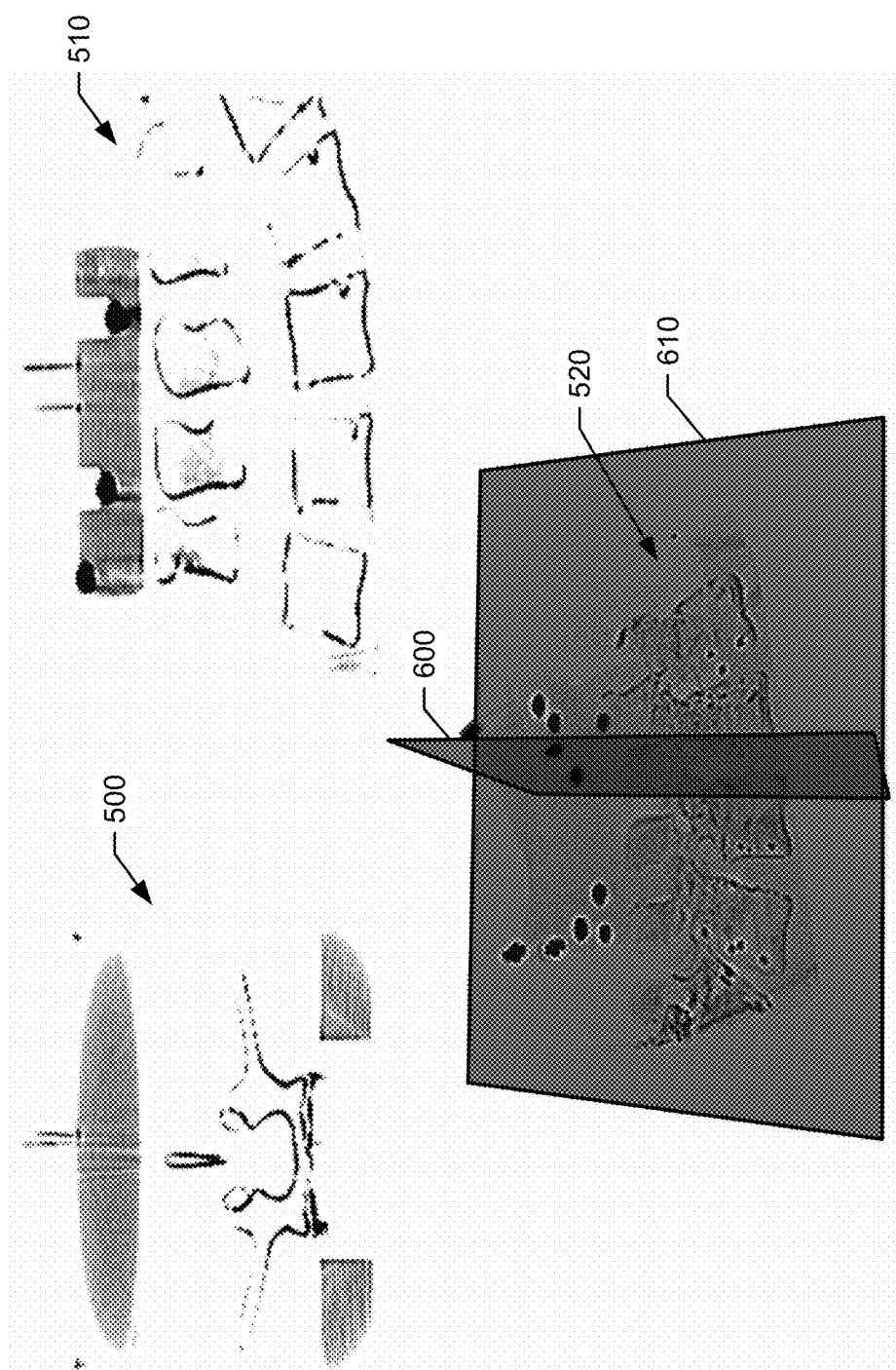
FIG. 6 illustrates an XR headset view of two graphical objects which are displayed with respective poses defined to visually illustrate to the user virtual cross-sectional planes extending through the 3D graphical model of FIG. 5 that correspond to the anatomical structure of the axial and sagittal 2D medical image slices of FIG. 5, in accordance with some embodiments.

Geometric Correspondence Visualization Between 2D Scan Slices and 3D Graphical Model FIG. 6 illustrates an XR headset view of two graphical objects 600 and 610 which are displayed with respective poses defined to visually illustrate to the user virtual cross-sectional planes extending through the 3D graphical model 520 of FIG. 5 that correspond to the anatomical structure of the axial and sagittal 2D medical image slices 500 and 510, respectively, of FIG. 5, in accordance with some embodiments.

Referring to FIG. 6, the graphical object 600 is displayed as a cross-sectional plane that extends through the 3D graphical model 520 with a pose that corresponds to where the 2D axial medical image slice 500 slices through the anatomical structure of the 3D graphical model 520. Similarly, the other graphical object 610 is displayed as another cross-sectional plane that extends through the 3D graphical model 520 with a pose that corresponds to where the 2D sagittal medical image slice 610 slices through the anatomical structure of the 3D graphical model 520. In this manner, a user wearing the XR headset is able to intuitively visualize the geometric relationship between the axial and sagittal 2D medical image slices 500 and 510, respectively, and the anatomical structure of the 3D graphical model 520.

Figure 7:
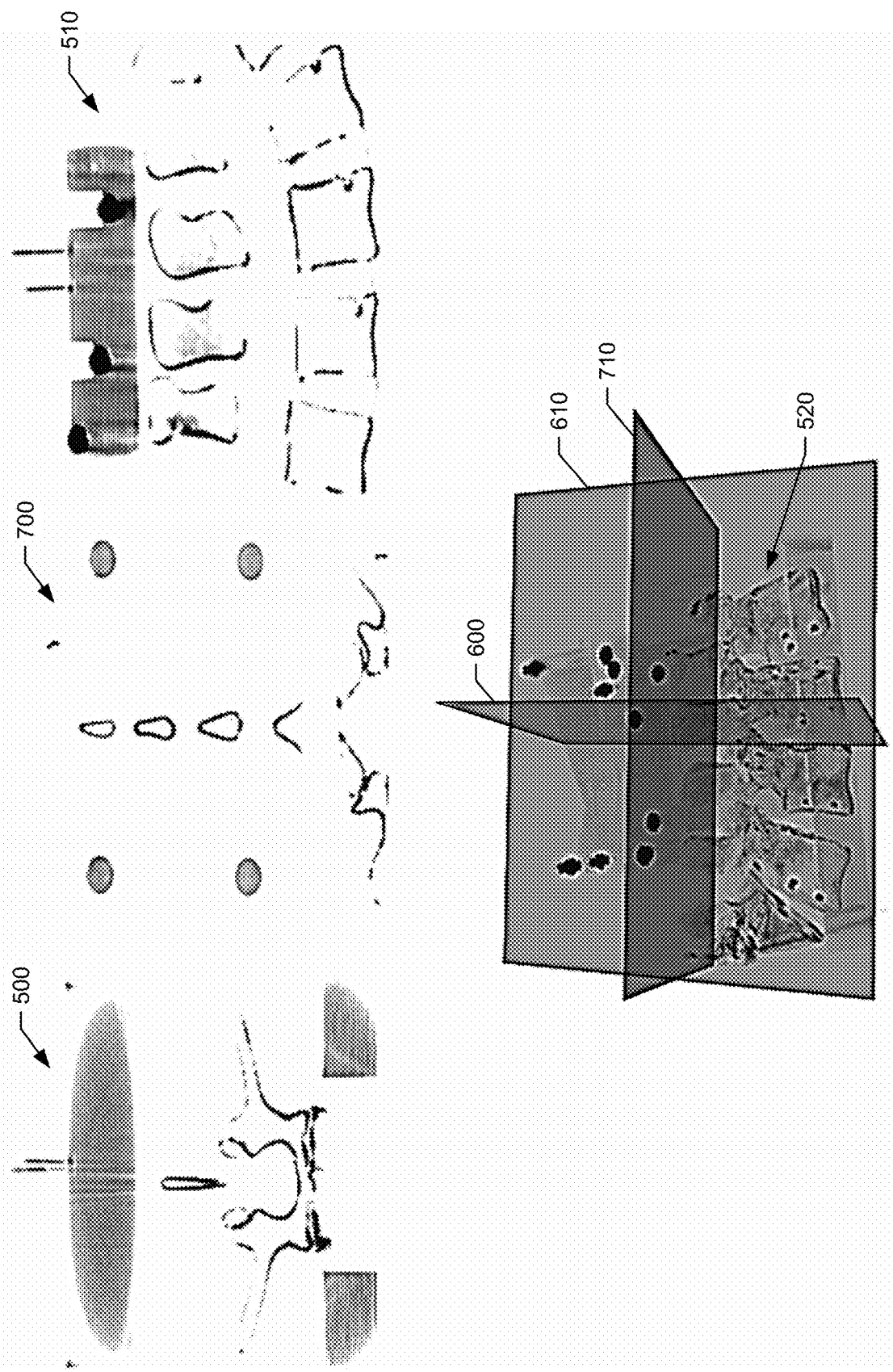
FIG. 7 illustrates another XR headset view that adds to the display of FIG. 6 a coronal 2D medical image slice of the anatomical structure of the patient and further adds a corresponding graphical object which is displayed with a pose that is defined to visually illustrate to the user a virtual cross-sectional plane extending through the 3D graphical model of FIG. 5 that corresponds to the anatomical structure of the coronal 2D medical image slice, in accordance with some embodiments.

FIG. 7 illustrates another XR headset view that adds to the display of FIG. 6. A coronal 2D medical image slice 700 of the anatomical structure of the patient is displayed through the XR headset along with the axial medical image slice 500 and the sagittal 2D medical image slice 510. The XR headset is also controlled to display a graphical object 710 with a pose that is defined to visually illustrate to the user a virtual cross-sectional plane extending through the 3D graphical model 520 that corresponds to the anatomical structure of the coronal 2D medical image slice, in accordance with some embodiments.

Figure 12:
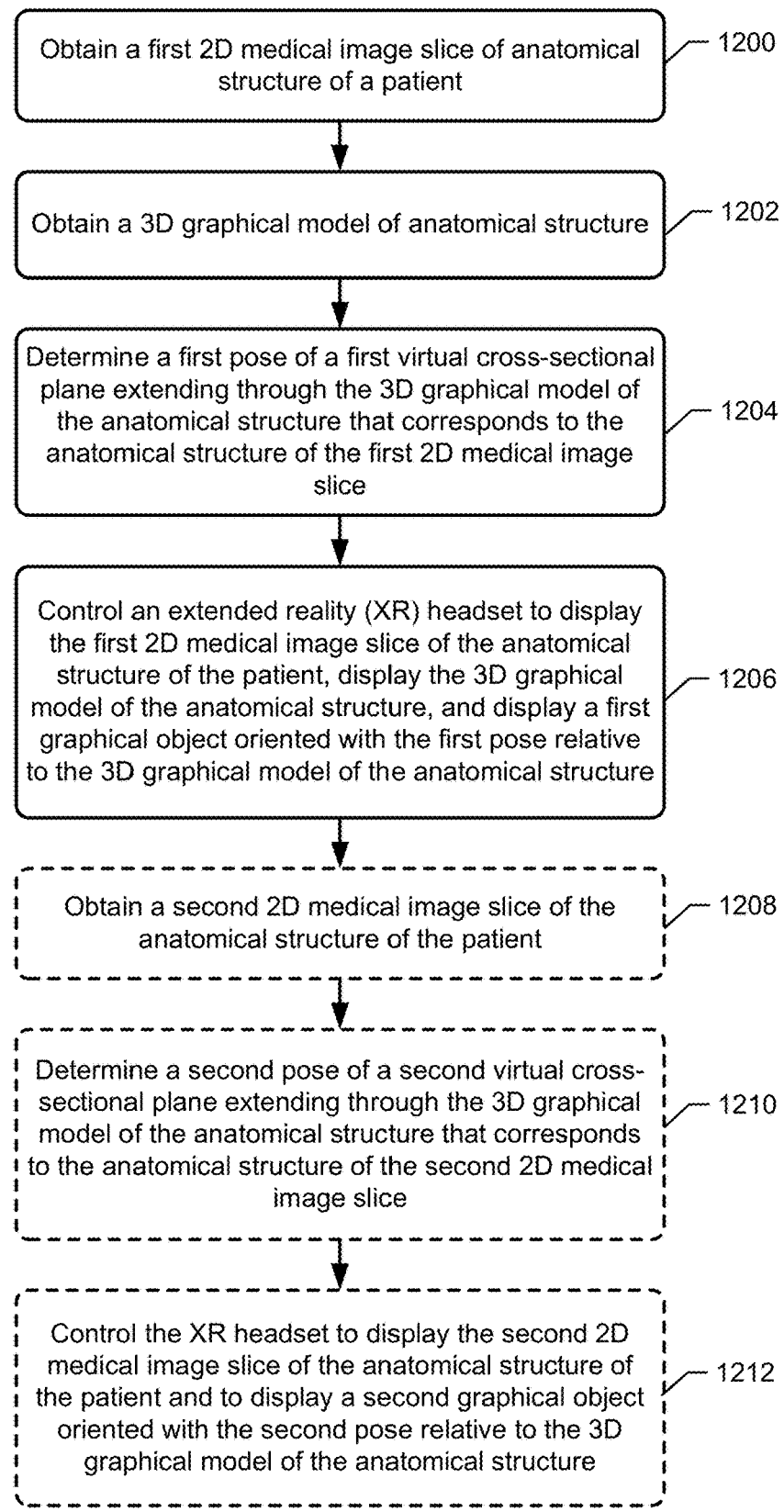
FIGS. 12-15 illustrates flowcharts of operations by a navigated surgery system in accordance with some embodiments.

Although operations have been described in the context of the example FIGS. 5 through 7, embodiments of the present disclosure are not limited thereto. More general corresponding operations are now explained with reference to FIG. 12. FIG. 12 illustrates a flowchart of operations by a navigated surgery system in accordance with some embodiments. Embodiments are not limited to the order of operations shown in FIG. 12 or to including all illustrated operations. For example, at least operations 1208 through 1212 are optional.

Referring to FIG. 12, the navigated surgery system operates to obtain 1200 a first 2D medical image slice of anatomical structure of a patient, such as one of the slices 500, 510, and 700, from a medical image scanner or image database. The system obtains 1202 a 3D graphical model of anatomical structure, such as the model 520, from a medical image scanner, image database, or model database or generator. The system determines 1204 a first pose of a first virtual cross-sectional plane extending through the 3D graphical model of the anatomical structure that corresponds to the anatomical structure of the first 2D medical image slice. The system controls an XR headset to display the first 2D medical image slice of the anatomical structure of the patient, display the 3D graphical model of the anatomical structure, and display a first graphical object oriented with the first pose relative to the 3D graphical model of the anatomical structure.

The navigated surgery system may control the XR headset to display a graphical representation of a plane overlaid with the first pose on the 3D graphical model of the anatomical structure, such as the plane 610 overlaid on the model 520. The graphical representation of the plane may be provided to the XR headset for display as a shaded and/or colored box overlaid with the first pose on the 3D graphical model of the anatomical structure, such as the shaded plane 610 overlaid on the model 520.

The navigated surgery system may display more than one 2D medical image slice such as illustrated in FIGS. 5 through 7. Accordingly, the system may obtain 1208 a second 2D medical image slice of the anatomical structure of the patient, wherein the first 2D medical image slice is an angularly offset image slice of the anatomical structure of the patient relative to the second 2D medical image slice, and determine 1210 a second pose of a second virtual cross-sectional plane extending through the 3D graphical model of the anatomical structure that corresponds to the anatomical structure of the second 2D medical image slice. The system can then control 1212 the XR headset to display the second 2D medical image slice of the anatomical structure of the patient and to display a second graphical object oriented with the second pose relative to the 3D graphical model of the anatomical structure.

The first 2D medical image slice may be an axial image slice of the anatomical structure of the patient and the second 2D medical image slice may be a sagittal image slice of the anatomical structure of the patient, such as those illustrated in FIGS. 5 through 7.

The navigated surgery system may further operate to control the XR headset to display a graphical representation of a first plane, e.g., 600 in FIG. 7, overlaid with the first pose on the 3D graphical model of the anatomical structure, and control the XR headset to display a second graphical representation of a second plane, e.g., 620 in FIG. 7, overlaid with the second pose on the 3D graphical model of the anatomical structure.

The navigated surgery system may further operate to control the XR headset to use a first color and/or shading to render at least part of the first 2D medical image slice of the anatomical structure of the patient and to render at least part of the graphical representation of the first plane for display, and control the XR headset to use a second color and/or shading, which is different from the first color and/or shading, to render at least part of the second 2D medical image slice of the anatomical structure of the patient and to render at least part of the graphical representation of the second plane for display. In this manner, the user is able to intuitively understand how each of the two 2D medical image slices geometrically correspond to cross-sectional slices through the 3D graphical model of the anatomical structure.

The navigated surgery system may further operate to obtain a third 2D medical image slice of the anatomical structure of the patient, where the third 2D medical image slice is an angularly offset image slice of the anatomical structure of the patient relative to the second and third 2D medical image slices. The third 2D medical image slice may be a coronal image slice of the anatomical structure of the patient. The system determines a third pose of a third virtual cross-sectional plane extending through the 3D graphical model of the anatomical structure that corresponds to the anatomical structure of the third 2D medical image slice. The system controls the XR headset to display the third 2D medical image slice, e.g., 700 in FIG. 7, of the anatomical structure of the patient and to display a third graphical object, e.g., 710 in FIG. 7, oriented with the third pose relative to the 3D graphical model of the anatomical structure.

Tool-Centric Visualization of 2D Scan Slice

During a navigated surgical procedure, the standard axial 2D image slice and/or sagittal 2D image slice visualization may be swapped for a tool-centric visualization whereby perpendicular image slice(s) are selected among image slices forming an image volume based on the tip of a tracked surgical instrument (tool). The image slice(s) can be displayed as overlay(s) on the 3D graphical model of the anatomical structure and/or on the patient viewed through a see-through screen of the XR headset.

Figure 8:
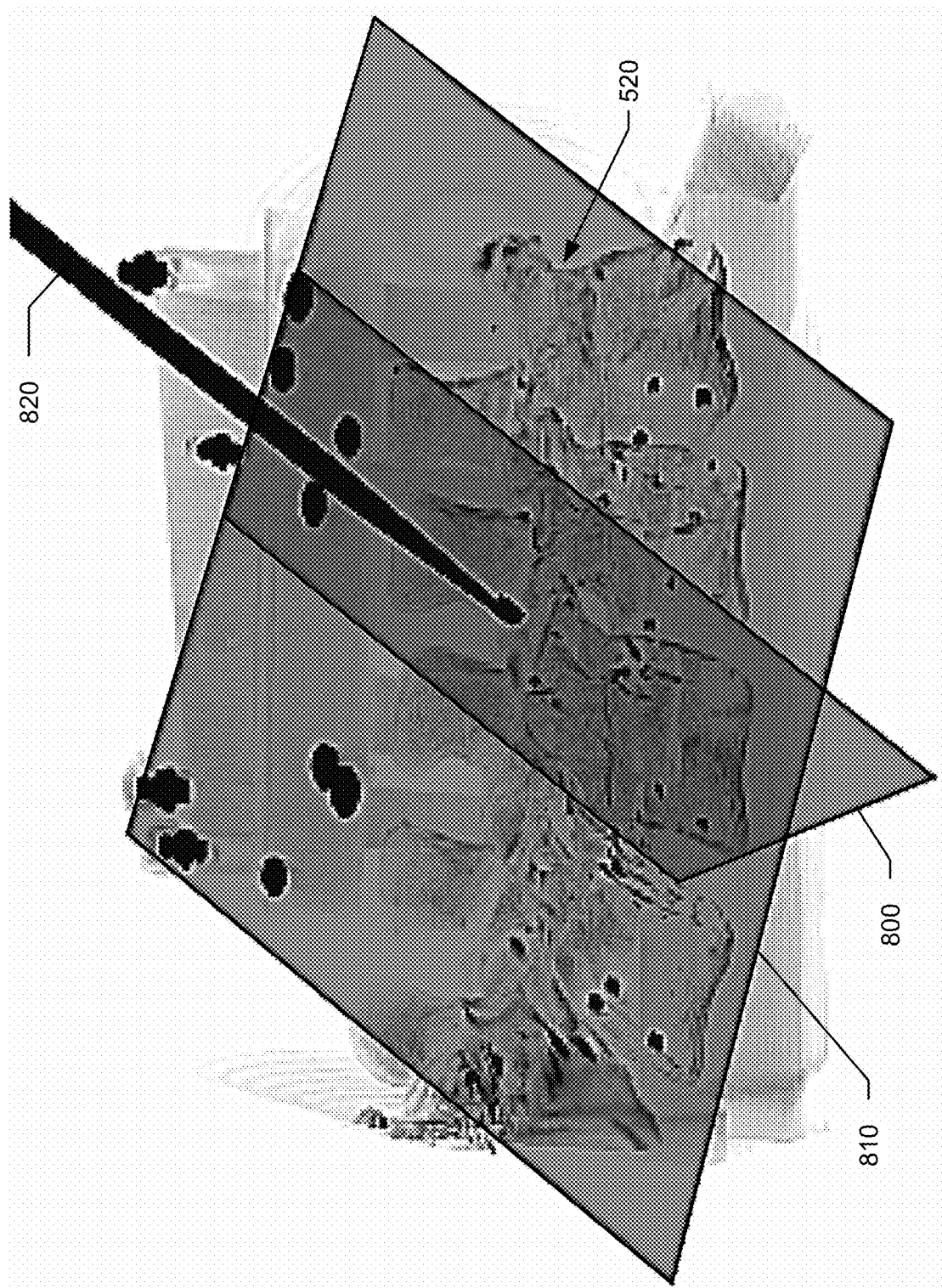
FIG. 8 illustrates another XR headset view of a 3D graphical model of anatomical structure with axial and sagittal 2D medical image slice of the anatomical structure of the patient being dynamically selected and posed responsive to tracking pose of a tip of a tool, in accordance with some embodiments.
Figure 13:
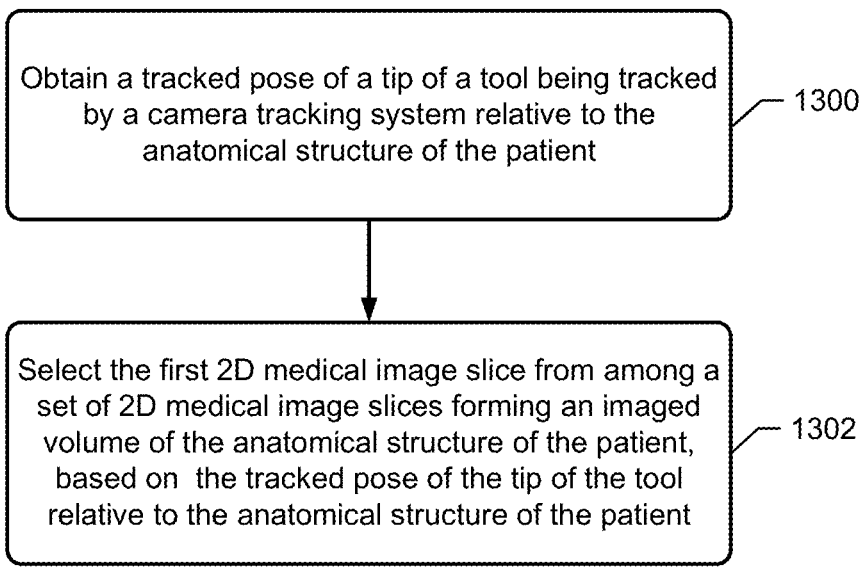

FIG. 8 illustrates an XR headset view of axial and sagittal 2D image slices 800 and 810, respectively, which are displayed with poses defined to visually illustrate to the user virtual cross-sectional planes extending through the 3D graphical model 520 of FIG. 5, and where the 2D image slices are dynamically selected and posed responsive to tracking pose of a tip of a tool 820 (instrument, etc.), in accordance with some embodiments. FIG. 13 illustrates a flowchart of corresponding operations by a navigated surgery system in accordance with some embodiments.

Referring to FIGS. 8 and 13, the navigated surgery system is operative to obtain 1300 a tracked pose of a tip of a tool 820 being tracked by a camera tracking system relative to the anatomical structure of the patient. The system operates to select 1302 a 2D medical image slice 810 from among a set of 2D medical image slices forming an imaged volume of the anatomical structure of the patient, based on the tracked pose of the tip of the tool 820 relative to the anatomical structure of the patient.

Thus, for example, as a surgeon moves the tool tip within the displayed spine of the 3D graphical model 520, the navigated surgery system responds to the updated pose locations of the tool tip by selecting, from among the set of 2D image slices, and displaying through the XR headset corresponding 2D image slices. In this manner, the surgeon can dynamically reposition the tool 820 to see corresponding 2D image slices of the patient's anatomy, i.e., spine illustrated in FIG. 8.

Fixed-Plane 3D Graphical Model Rotation

Another operational embodiment aids a surgeon with visualization by keeping the slice planes fixed while allowing manual rotation of the 3D graphical model 610. The operations allow the surgeon to spin the 3D graphical model 610 around while maintaining fixed viewing planes of the axial and sagittal 2D image slices.

Figure 9A:
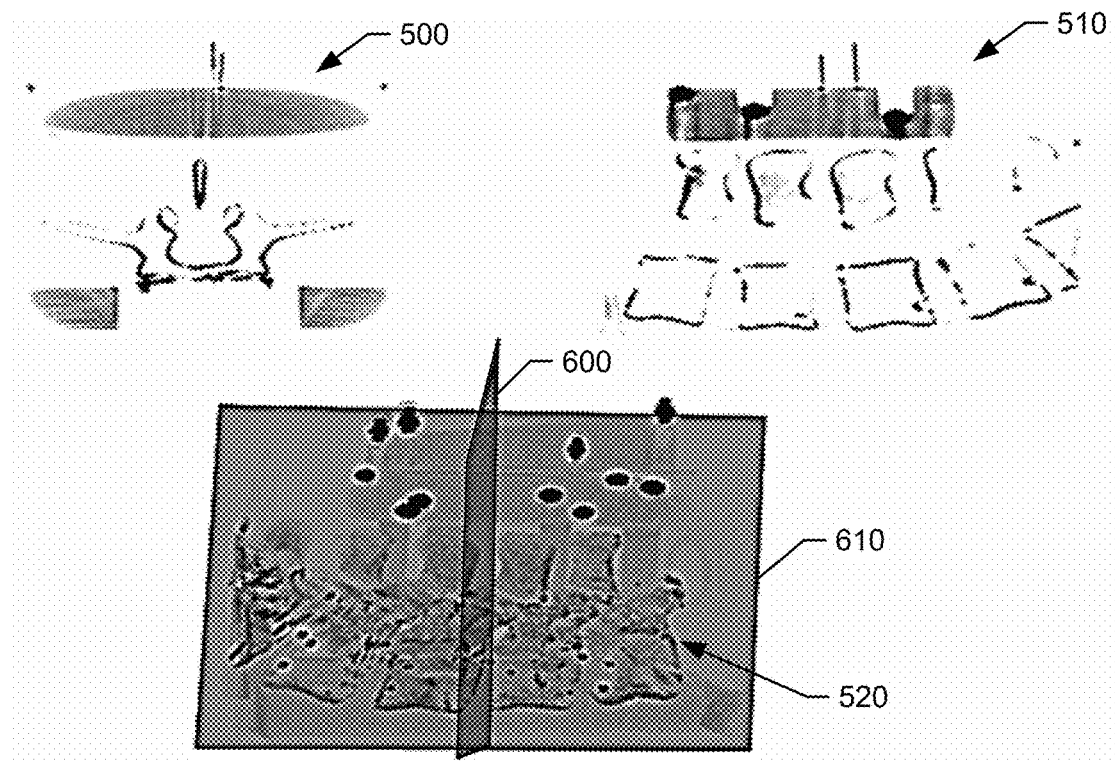
FIGS. 9A and 9B illustrate two alternative views displayed through the XR headset of a starting orientation and 90 degree rotated orientation, respectively, of the axial and sagittal 2D medical image slices of FIG. 5 and graphical objects being displayed with respective poses defined to visually illustrate to the user virtual cross-sectional planes extending through the 3D graphical model that correspond to the anatomical structure of the viewed axial and sagittal 2D medical image slices, in accordance with some embodiments.

FIG. 9A illustrates a view displayed through the XR headset of a starting orientation of the axial medical image slice 520 and the sagittal 2D image slice 510 and graphical objects 600 and 610 being displayed with respective poses defined to visually illustrate to the user virtual cross-sectional planes extending through the 3D graphical model 610 that correspond to the anatomical structure of the viewed axial and sagittal 2D image slices, in accordance with some embodiments. The graphical object 600 is illustrated as the virtual cross-sectional plane corresponding to the axial medical image slice 520. The other graphical object 610 is illustrated as the virtual cross-sectional plane corresponding to the sagittal 2D image slice 510.

Figure 9B:
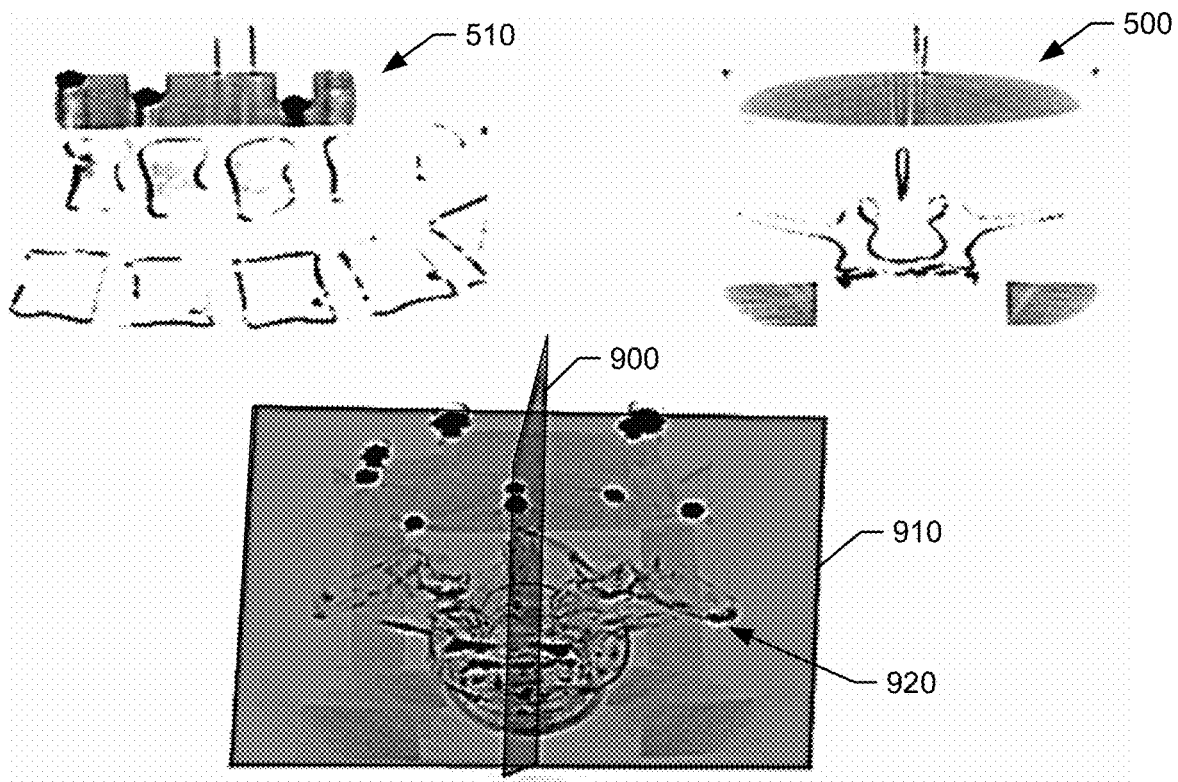

In FIG. 9B the 3D graphical model 610 is rotated 90 around the vertical axis to be illustrated as viewed model 920, which effectively switches the axial slice 500 view and the sagittal slice 510 view. While rotating between these points, the surgeon is able to view all intermediate slice orientations with a clear and intuitive visualization. FIG. 9B illustrates a view displayed through the XR headset of a 90 degree rotated orientation of the axial medical image slice 520 and the sagittal 2D image slice 510, and graphical objects 910 and 900 being displayed with respective poses defined to visually illustrate to the user virtual cross-sectional planes extending through the 90 degree rotated orientation of the 3D graphical model 920, in accordance with some embodiments. The graphical object 910 is illustrated as the virtual cross-sectional plane corresponding to the axial medical image slice 500. The other graphical object 900 is illustrated as the virtual cross-sectional plane corresponding to the sagittal 2D image slice 510.

A corresponding operation by the navigated surgery system can include, responding to a rotation command from a user by controlling the XR headset to display an angularly rotated view of the 3D graphical model of the anatomical structure while displaying the first graphical object oriented with the first pose.

2D Image Slice Orientation Visualization

Some other embodiments are directed to displaying further information which enables visualization of the orientations of the 2D image slices. Sagittal image slices may be flipped in order to match the orientation from which a surgeon is viewing the patient's spine or other anatomy, and the orientation of the axial 2D image slices can then be difficult to perceive because the axial 2D image slices have few asymmetries. To enable more intuitive and accurate visualization of the corresponding 2D image slice orientations, overlays can be shaded and/or colored to visually indicate the orientation of the 2D image slice. The current orientation of the 2D image slice can be shown with an overlay, and if viewed from behind (or if the 2D image slice view is flipped) the overlay can be rendered as a hollow outline, or vice versa.

FIGS. 10A, 10B, 10C, and 10D illustrate four alternative views displayed through the XR headset of an axial unmirrored and sagittal unmirrored view, an axial unmirrored and sagittal mirrored view, an axial mirrored and sagittal unmirrored view, and an axial mirrored and sagittal mirrored view, respectively, and graphical objects being displayed with respective poses defined to visually illustrate to the user virtual cross-sectional planes extending through the 3D graphical model, in accordance with some embodiments.

Figure 10A:
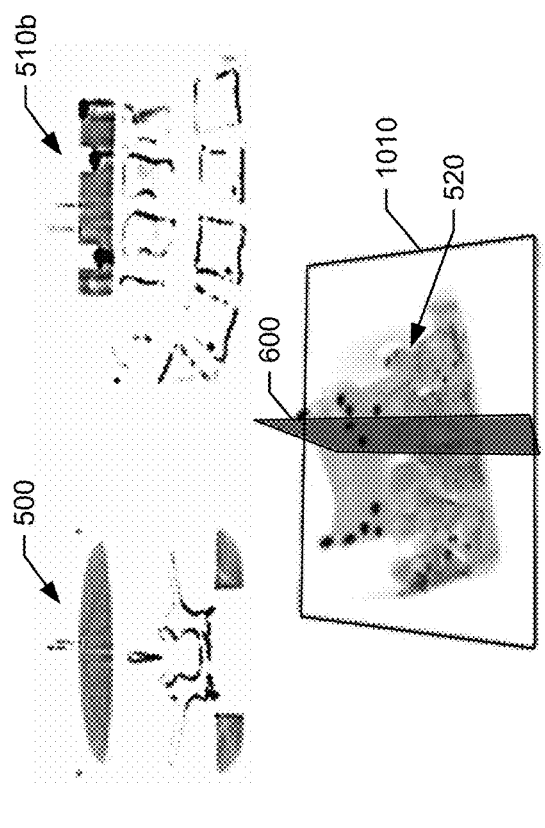
FIGS. 10A, 10B, 10C, and 10D illustrate four alternative views displayed through the XR headset of an axial unmirrored and sagittal unmirrored view, an axial unmirrored and sagittal mirrored view, an axial mirrored and sagittal unmirrored view, and an axial mirrored and sagittal mirrored view, respectively, and graphical objects being displayed with respective poses defined to visually illustrate to the user virtual cross-sectional planes extending through the 3D graphical model, in accordance with some embodiments.
Figure 10B:
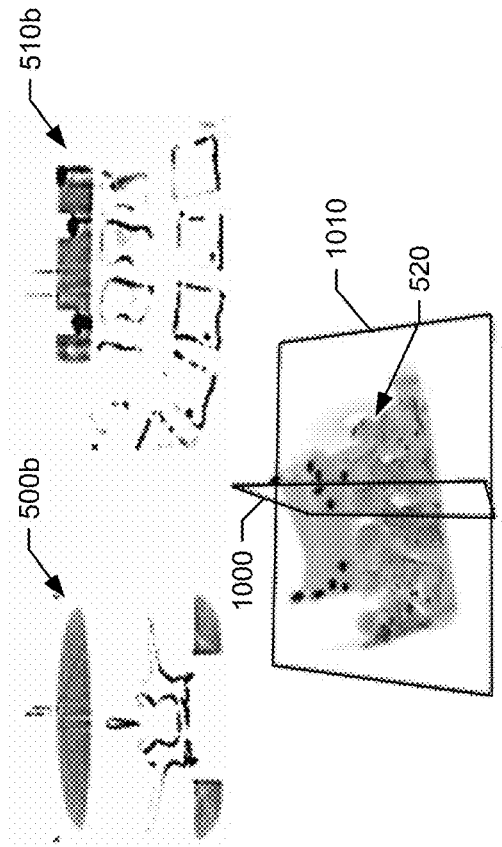
Figure 10C:
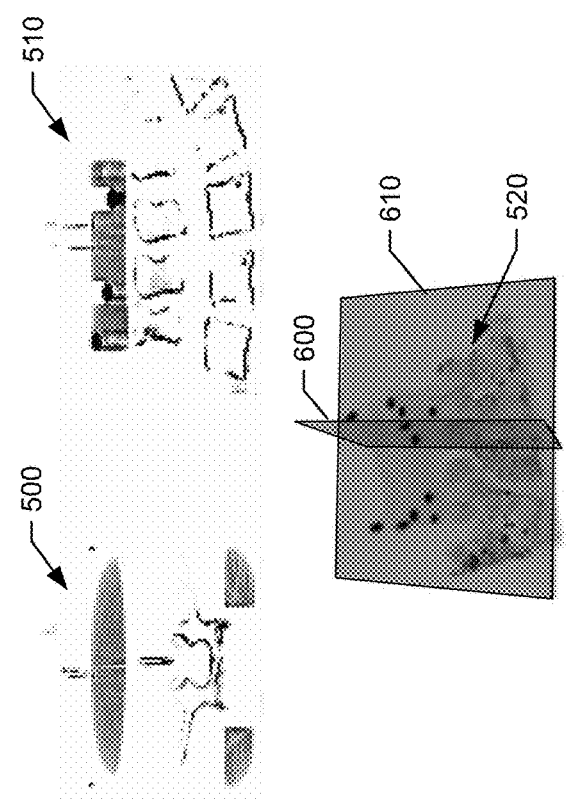
Figure 10D:
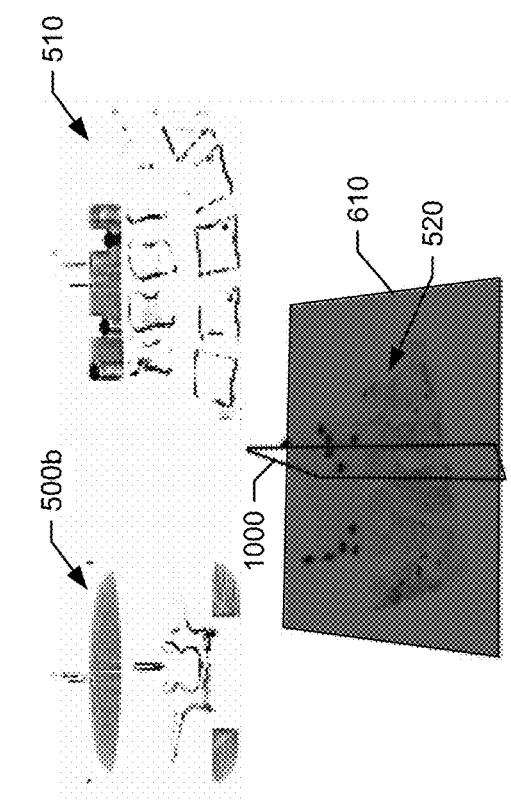
Figure 11:
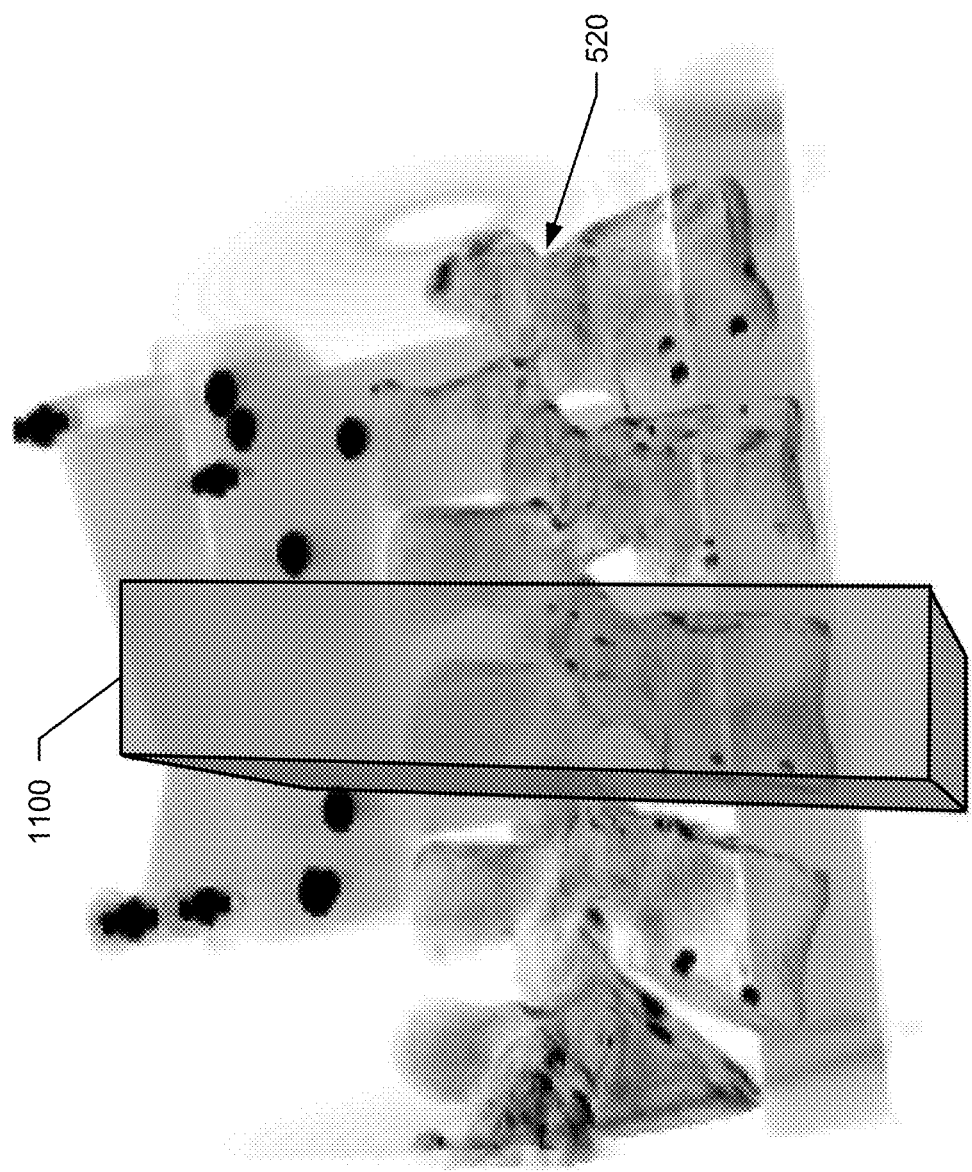
FIG. 11 illustrates the XR headset view of a 3D graphical object posed and extending to overly a region of the 3D graphical model corresponding to where a surgical procedure is to be performed on the anatomical structure of the patient, in accordance with some embodiments.

More particularly, FIG. 10A illustrates the axial unmirrored and sagittal unmirrored view in which the cross-sectional objects 600 and 610 are both shaded and/or colored. FIG. 10B illustrates the axial unmirrored and sagittal mirrored view in which the cross-sectional object 1010 corresponding to the sagittal 2D image slice is not shaded and/or colored to indicate it is a mirrored view. FIG. 10C illustrates the axial mirrored and sagittal unmirrored view in which the cross-sectional object 1000 corresponding to the axial 2D image slice is not shaded and/or colored to indicate it is a mirrored view. FIG. 10D illustrates the axial mirrored and sagittal mirrored view in which the cross-sectional object 1000 corresponding to the axial 2D image slice is not shaded and/or colored to indicate it is a mirrored view and in which the cross-sectional object 1010 corresponding to the sagittal 2D image slice is not shaded and/or colored to indicate it is a mirrored view.

Accordingly, while wearing the XR headset, the surgeon can move around the patient to view an overlay from an opposite side which uses an opposite shading and/or color effect to visually illustrate the different viewing perspectives. In some embodiments the operations for the shading or hollow representations are reversed, and/or a visual indication (queue) is added, e.g., as a star or other symbol in the upper left corner of the corresponding slices. In some embodiments a gradient across the slice background is used to intuitively indicate the viewed directionality.

Figure 14:
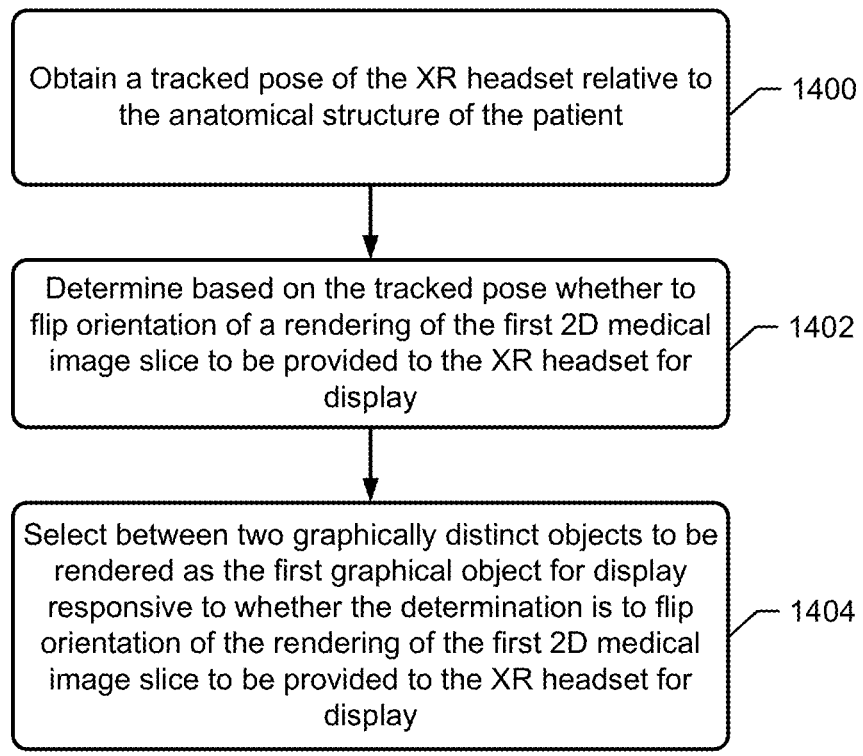

Corresponding operations that may be performed by the navigated surgery system are illustrated in the flowchart of FIG. 14. Referring to FIG. 14, the operations obtain 1400 a tracked pose of the XR headset relative to the anatomical structure of the patient. The operations determine 1402 based on the tracked pose whether to flip orientation of a rendering of the first 2D medical image slice to be provided to the XR headset for display. The operations then select 1404 between two graphically distinct objects to be rendered as the first graphical object for display responsive to whether the determination is to flip orientation of the rendering of the first 2D medical image slice to be provided to the XR headset for display.

Current Level Visualization

During surgery, the active vertebral level is always important for a surgeon or other user to know. Incorrectly identifying levels or associating a level on the 2D image scan with the wrong level on a patient can be catastrophic during surgery. 3D graphical model visualizations can help resolve this issue. The navigated surgery system may operate to identify the selected (active) level in the 2D image scan and display a highlighted zone (or other 3D graphical object) on the currently selected level. When surgical implants or tracked instruments appear on the wrong level, then such improper location (pose) will be immediately visually recognizable by the surgeon because the implants and instruments would appear outside of the highlighted zone. These operations enable such possible mistakes to be more intuitively and accurately detected and corrected.

Figure 15:
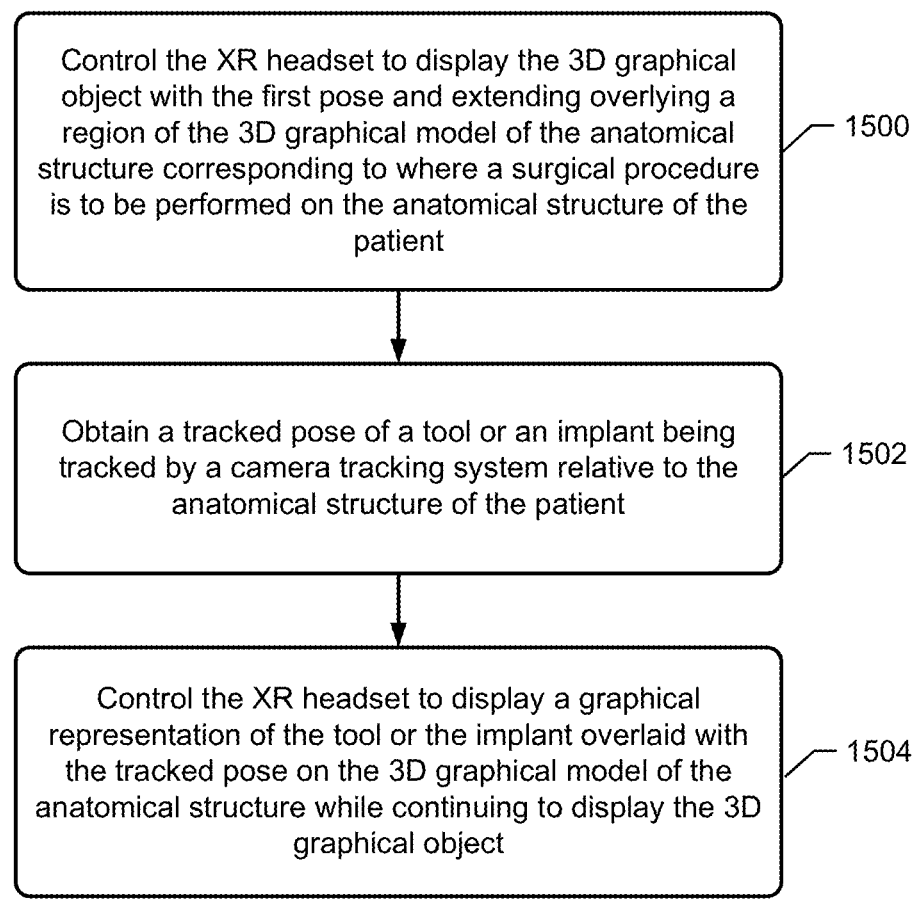

Corresponding operations that may be performed by the navigated surgery system are illustrated in the flowchart of FIG. 15. Referring to FIG. 15, the operations control 1500 the XR headset to display a 3D graphical object 1100 with a pose and extending to overly a region of the 3D graphical model of the anatomical structure corresponding to where a surgical procedure is to be performed on the anatomical structure of the patient. In the particular example of FIG. 15, 3D graphical object 1100 is rendered as a shaded 3D rectangular object that is posed to correspond to a level of the spine where a surgical procedure is to be performed. The operations obtain 1502 a tracked pose of a tool or an implant being tracked by a camera tracking system relative to the anatomical structure of the patient, e.g., spine illustrated in the 3D graphical model 520. The operations control 1504 the XR headset to display a graphical representation of the tool or the implant overlaid with the tracked pose on the 3D graphical model 520 of the anatomical structure while continuing to display the 3D graphical object 1100. In this manner, a wearer of the XR headset can visually determine in an intuitive manner whether the tool or implant is presently positioned and oriented (e.g., posed) at the correct level of the spine.

Example Surgical System

Figure 16:
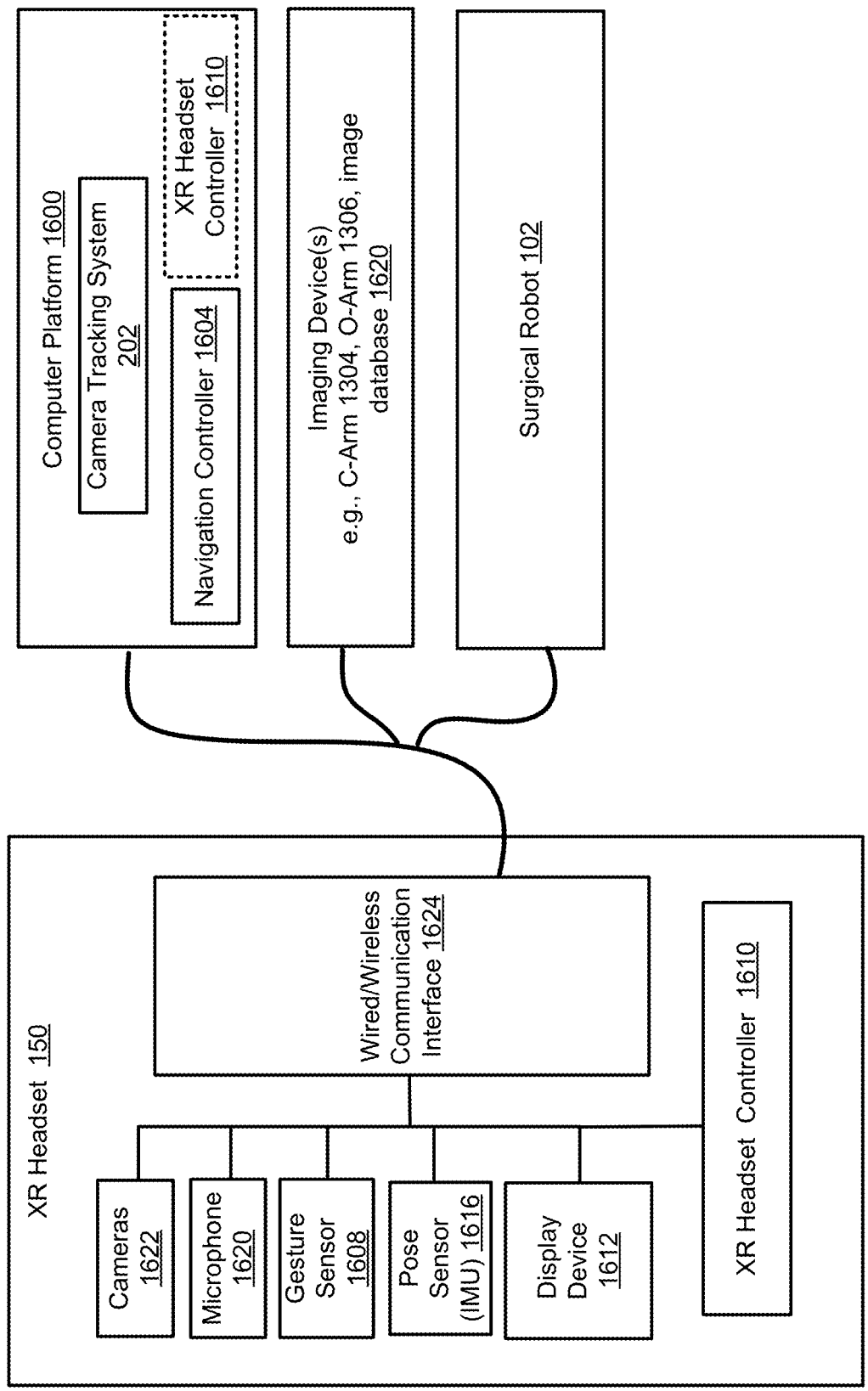
FIG. 16 illustrates a block diagram of a navigated surgery system that includes an XR headset, a computer platform, and a camera tracking system component which are operative in accordance with some embodiments.

FIG. 16 illustrates a block diagram of a surgical system that includes an XR headset 150, a computer platform 1600, imaging devices, and a surgical robot 102 which are configured to operate in accordance with various embodiments.

The imaging devices may include the C-arm imaging device 1304, the O-arm imaging device 1306, and/or a patient image database 1620. The XR headset 150 provides an improved human interface for performing navigated surgical procedures. The XR headset 150 can be configured to provide functionalities, e.g., via the computer platform 1600, that include without limitation any one or more of: identification of hand gesture based commands, display XR graphical objects on a display device 1612. The display device 1612 may a video projector, flat panel display, etc. The user can view the XR graphical objects as an overlay anchored to particular real-world objects viewed through a see-through display screen. The XR headset 150 may additionally or alternatively be configured to display on the display device 1612 video streams from cameras mounted to one or more XR headsets 150 and other cameras.

Electrical components of the XR headset 150 can include a plurality of cameras 1622, a microphone 1620, a gesture sensor 1618, a pose sensor (e.g., inertial measurement unit (IMU)) 1616, the display device 1612, and a wireless/wired communication interface 1624. The cameras 1622 of the XR headset 150 may be visible light capturing cameras, near infrared capturing cameras, or a combination of both.

The cameras 1622 may be configured to operate as the gesture sensor 1618 by tracking for identification user hand gestures performed within the field of view of the camera(s) 1622. Alternatively the gesture sensor 1618 may be a proximity sensor and/or a touch sensor that senses hand gestures performed proximately to the gesture sensor 1618 and/or senses physical contact, e.g. tapping on the sensor 1618 or its enclosure. The pose sensor 1616, e.g., IMU, may include a multi-axis accelerometer, a tilt sensor, and/or another sensor that can sense rotation and/or acceleration of the XR headset 150 along one or more defined coordinate axes. Some or all of these electrical components may be contained in a head-worn component enclosure or may be contained in another enclosure configured to be worn elsewhere, such as on the hip or shoulder.

As explained above, a surgical system includes a camera tracking system 202 which may be part of a computer platform 1600 that can also provide functionality of a navigation controller 1604 and/or of a XR headset controller 1610. The surgical system may include the imaging devices and/or a surgical robot 102. The navigation controller 1604 can be configured to provide visual navigation guidance to an operator for moving and positioning a surgical tool relative to patient anatomical structure based on a surgical plan, e.g., from a surgical planning function, defining where a surgical procedure is to be performed using the surgical tool on the anatomical structure and based on a pose of the anatomical structure determined by the camera tracking system 202. The navigation controller 1604 may be further configured to generate navigation information based on a target pose for a surgical tool, a pose of the anatomical structure, and a pose of the surgical tool and/or an end effector of the surgical robot 102, where the steering information is used to display information through the XR headset 150 to indicate where the surgical tool and/or the end effector of the surgical robot 102 should be moved to perform the surgical plan.

The electrical components of the XR headset 150 can be operatively connected to the electrical components of the computer platform 1600 through a wired/wireless interface 1624. The electrical components of the XR headset 150 may be operatively connected, e.g., through the computer platform 1600 or directly connected, to various imaging devices, e.g., the C-arm imaging device 1304, the I/O-arm imaging device 1306, the patient image database 1620, and/or to other medical equipment through the wired/wireless interface 1624.

The surgical system further includes at least one XR headset controller 1610 (also referred to as "XR headset controller" for brevity) that may reside in the XR headset 150, the computer platform 1600, and/or in another system component connected via wired cables and/or wireless communication links. Various functionality is provided by software executed by the XR headset controller 1610. The XR headset controller 1610 is configured to receive information from the camera tracking system 202 and the navigation controller 1604, and to generate an XR image based on the information for display on the display device 1612.

The XR headset controller 1610 can be configured to operationally process signaling from the cameras 1622, the microphone 1620, and/or the pose sensor 1616, and is connected to display XR images on the display device 1612 for user viewing. Thus, the XR headset controller 1610 illustrated as a circuit block within the XR headset 150 is to be understood as being operationally connected to other illustrated components of the XR headset 150 but not necessarily residing within a common housing or being otherwise transportable by the user. For example, the XR headset controller 1610 may reside within the computer platform 1600 which, in turn, may reside within a housing of the surgical robot 102, the camera tracking system 202, etc.

Further Definitions and Embodiments

In the above-description of various embodiments of present inventive concepts, it is to be understood that the terminology used herein is for the purpose of describing particular embodiments only and is not intended to be limiting of present inventive concepts. Unless otherwise defined, all terms (including technical and scientific terms) used herein have the same meaning as commonly understood by one of ordinary skill in the art to which present inventive concepts belongs. It will be further understood that terms, such as those defined in commonly used dictionaries, should be interpreted as having a meaning that is consistent with their meaning in the context of this specification and the relevant art and will not be interpreted in an idealized or overly formal sense expressly so defined herein.

When an element is referred to as being "connected", "coupled", "responsive", or variants thereof to another element, it can be directly connected, coupled, or responsive to the other element or intervening elements may be present. In contrast, when an element is referred to as being "directly connected", "directly coupled", "directly responsive", or variants thereof to another element, there are no intervening elements present. Like numbers refer to like elements throughout. Furthermore, "coupled", "connected", "responsive", or variants thereof as used herein may include wirelessly coupled, connected, or responsive. As used herein, the singular forms "a", "an" and "the" are intended to include the plural forms as well, unless the context clearly indicates otherwise. Well-known functions or constructions may not be described in detail for brevity and/or clarity. The term "and/or" includes any and all combinations of one or more of the associated listed items.

It will be understood that although the terms first, second, third, etc. may be used herein to describe various elements/operations, these elements/operations should not be limited by these terms. These terms are only used to distinguish one element/operation from another element/operation. Thus, a first element/operation in some embodiments could be termed a second element/operation in other embodiments without departing from the teachings of present inventive concepts. The same reference numerals or the same reference designators denote the same or similar elements throughout the specification.

As used herein, the terms "comprise", "comprising", "comprises", "include", "including", "includes", "have", "has", "having", or variants thereof are open-ended, and include one or more stated features, integers, elements, steps, components or functions but does not preclude the presence or addition of one or more other features, integers, elements, steps, components, functions or groups thereof. Furthermore, as used herein, the common abbreviation "e.g.", which derives from the Latin phrase "exempli gratia," may be used to introduce or specify a general example or examples of a previously mentioned item, and is not intended to be limiting of such item. The common abbreviation "i.e.", which derives from the Latin phrase "id est," may be used to specify a particular item from a more general recitation.

Example embodiments are described herein with reference to block diagrams and/or flowchart illustrations of computer-implemented methods, apparatus (systems and/or devices) and/or computer program products. It is understood that a block of the block diagrams and/or flowchart illustrations, and combinations of blocks in the block diagrams and/or flowchart illustrations, can be implemented by computer program instructions that are performed by one or more computer circuits. These computer program instructions may be provided to a processor circuit of a general purpose computer circuit, special purpose computer circuit, and/or other programmable data processing circuit to produce a machine, such that the instructions, which execute via the processor of the computer and/or other programmable data processing apparatus, transform and control transistors, values stored in memory locations, and other hardware components within such circuitry to implement the functions/acts specified in the block diagrams and/or flowchart block or blocks, and thereby create means (functionality) and/or structure for implementing the functions/acts specified in the block diagrams and/or flowchart block(s).

These computer program instructions may also be stored in a tangible computer-readable medium that can direct a computer or other programmable data processing apparatus to function in a particular manner, such that the instructions stored in the computer-readable medium produce an article of manufacture including instructions which implement the functions/acts specified in the block diagrams and/or flowchart block or blocks. Accordingly, embodiments of present inventive concepts may be embodied in hardware and/or in software (including firmware, resident software, microcode, etc.) that runs on a processor such as a digital signal processor, which may collectively be referred to as "circuitry," "a module" or variants thereof.

It should also be noted that in some alternate implementations, the functions/acts noted in the blocks may occur out of the order noted in the flowcharts. For example, two blocks shown in succession may in fact be executed substantially concurrently or the blocks may sometimes be executed in the reverse order, depending upon the functionality/acts involved. Moreover, the functionality of a given block of the flowcharts and/or block diagrams may be separated into multiple blocks and/or the functionality of two or more blocks of the flowcharts and/or block diagrams may be at least partially integrated. Finally, other blocks may be added/inserted between the blocks that are illustrated, and/or blocks/operations may be omitted without departing from the scope of inventive concepts. Moreover, although some of the diagrams include arrows on communication paths to show a primary direction of communication, it is to be understood that communication may occur in the opposite direction to the depicted arrows.

Many variations and modifications can be made to the embodiments without substantially departing from the principles of the present inventive concepts. All such variations and modifications are intended to be included herein within the scope of present inventive concepts. Accordingly, the above disclosed subject matter is to be considered illustrative, and not restrictive, and the appended examples of embodiments are intended to cover all such modifications, enhancements, and other embodiments, which fall within the spirit and scope of present inventive concepts. Thus, to the maximum extent allowed by law, the scope of present inventive concepts are to be determined by the broadest permissible interpretation of the present disclosure including the following examples of embodiments and their equivalents, and shall not be restricted or limited by the foregoing detailed description.

What is claimed is:

1. A method by a navigated surgery system, the method comprising:
    obtaining a first two-dimensional (2D) medical image slice of a portion of an internal anatomical structure of a patient;
    obtaining a three-dimensional (3D) graphical model of the internal anatomical structure;
    determining a first pose of a first virtual cross-sectional plane extending through the 3D graphical model of the internal anatomical structure, wherein the first virtual cross-sectional plane corresponds to the portion of the internal anatomical structure imaged by the first 2D medical image slice; and
    controlling an extended reality (XR) headset to simultaneously display on a display device the first 2D medical image slice of the internal anatomical structure of the patient, the 3D graphical model of the internal anatomical structure, and a first graphical object oriented with the first pose relative to the 3D graphical model of the internal anatomical structure,
    wherein the XR headset is configured to operate to track hand poses and gestures to enable gesture based interactions with virtual buttons and interfaces displayed through the XR headset and configured to interpret hand gesturing as defined commands.

2. The method of claim 1, further comprising:
    obtaining a second 2D medical image slice of the internal anatomical structure of the patient, wherein the first 2D medical image slice is an angularly offset image slice of the internal anatomical structure of the patient relative to the second 2D medical image slice;
    determining a second pose of a second virtual cross-sectional plane extending through the 3D graphical model of the internal anatomical structure that corresponds to the internal anatomical structure of the second 2D medical image slice; and
    controlling the XR headset to display the second 2D medical image slice of the internal anatomical structure of the patient and to display a second graphical object oriented with the second pose relative to the 3D graphical model of the internal anatomical structure.

3. The method of claim 1, further comprising:
    obtaining a tracked pose of a tip of a tool being tracked by a camera tracking system relative to the internal anatomical structure of the patient;
    selecting the first 2D medical image slice from among a set of 2D medical image slices forming an imaged volume of the internal anatomical structure of the patient, based on the tracked pose of the tip of the tool relative to the internal anatomical structure of the patient.

4. The method of claim 1, further comprising:
    responsive to a rotation command from a user, controlling the XR headset to display an angularly rotated view of the 3D graphical model of the internal anatomical structure while displaying the first graphical object oriented with the first pose.

5. The method of claim 1, further comprising:
    obtaining a tracked pose of the XR headset relative to the internal anatomical structure of the patient;
    determining based on the tracked pose whether to flip orientation of a rendering of the first 2D medical image slice to be provided to the XR headset for display; and
    selecting between two graphically distinct objects to be rendered as the first graphical object for display responsive to whether the determination is to flip orientation of the rendering of the first 2D medical image slice to be provided to the XR headset for display.

6. The method of claim 1, further comprising:
    controlling the XR headset to display the first graphical object with the first pose and extending to overly a region of the 3D graphical model of the internal anatomical structure corresponding to where a surgical procedure is to be performed on the internal anatomical structure of the patient;

obtaining a tracked pose of a tool or an implant being tracked by a camera tracking system relative to the internal anatomical structure of the patient;

controlling the XR headset to display a graphical representation of the tool or the implant overlaid with the tracked pose on the 3D graphical model of the internal anatomical structure while continuing to display the first graphical object.

7. A method by a navigated surgery system comprising:

providing a computer program product comprising a non-transitory computer readable medium storing program instructions executable by at least one processor of the navigated surgery system to:

obtain a first two-dimensional (2D) medical image slice of an internal anatomical structure of a patient;

obtain a three-dimensional (3D) graphical model of the internal anatomical structure;

determine a first pose of a first virtual cross-sectional plane extending through the 3D graphical model of the internal anatomical structure that corresponds to the internal anatomical structure of the first 2D medical image slice; and control an extended reality (XR) headset to simultaneously display on a display device the first 2D medical image slice of the internal anatomical structure of the patient, the 3D graphical model of the internal anatomical structure, and a first graphical object oriented with the first pose relative to the 3D graphical model of the internal anatomical structure, wherein the XR headset is configured to operate to track hand poses and gestures to enable gesture-based interactions with virtual buttons and interfaces displayed through the XR headset and configured to interpret hand gesturing as defined commands.

8. The method of claim 7, further comprising:

obtaining a second 2D medical image slice of the internal anatomical structure of the patient, wherein the first 2D medical image slice is an angularly offset image slice of the internal anatomical structure of the patient relative to the second 2D medical image slice;

determining a second pose of a second virtual cross-sectional plane extending through the 3D graphical model of the internal anatomical structure that corresponds to the internal anatomical structure of the second 2D medical image slice; and controlling the XR headset to display the second 2D medical image slice of the internal anatomical structure of the patient and to display a second graphical object oriented with the second pose relative to the 3D graphical model of the internal anatomical structure.

9. The method of claim 7, further comprising:

obtaining a tracked pose of a tip of a tool being tracked by a camera tracking system relative to the internal anatomical structure of the patient;

selecting the first 2D medical image slice from among a set of 2D medical image slices forming an imaged volume of the internal anatomical structure of the patient, based on the tracked pose of the tip of the tool relative to the internal anatomical structure of the patient.

10. The method of claim 7, further comprising:

responsive to a rotation command from a user, controlling the XR headset to display an angularly rotated view of the 3D graphical model of the internal anatomical structure while displaying the first graphical object oriented with the first pose.

11. The method of claim 7, further comprising:

obtaining a tracked pose of the XR headset relative to the internal anatomical structure of the patient;

determining based on the tracked pose whether to flip orientation of a rendering of the first 2D medical image slice to be provided to the XR headset for display; and selecting between two graphically distinct objects to be rendered as the first graphical object for display responsive to whether the determination is to flip orientation of the rendering of the first 2D medical image slice to be provided to the XR headset for display.

12. The method of claim 7, further comprising:

controlling the XR headset to display the first graphical object with the first pose and extending to overly a region of the 3D graphical model of the internal anatomical structure corresponding to where a surgical procedure is to be performed on the internal anatomical structure of the patient;

obtaining a tracked pose of a tool or an implant being tracked by a camera tracking system relative to the internal anatomical structure of the patient;

controlling the XR headset to display a graphical representation of the tool or the implant overlaid with the tracked pose on the 3D graphical model of the internal anatomical structure while continuing to display the first graphical object.

* * * * *